United States Patent
Fanson et al.

(10) Patent No.: US 11,896,321 B2
(45) Date of Patent: Feb. 13, 2024

(54) SYSTEMS AND METHODS TO REGISTER PATIENT ANATOMY OR TO DETERMINE AND PRESENT MEASUREMENTS RELATIVE TO PATIENT ANATOMY

(71) Applicant: INTELLIJOINT SURGICAL INC., Kitchener (CA)

(72) Inventors: Richard Tyler Fanson, Stoney Creek (CA); Eric Ryterski, Louisville, CO (US); Armen Garo Bakirtzian, Kitchener (CA); Andre Novomir Hladio, Waterloo (CA)

(73) Assignee: Intellijoint Surgical Inc., Kitchener (CA)

( * ) Notice: Subject to any disclaimer, the term of this patent is extended or adjusted under 35 U.S.C. 154(b) by 0 days.

(21) Appl. No.: 18/129,698

(22) Filed: Mar. 31, 2023

(65) Prior Publication Data
US 2023/0233267 A1    Jul. 27, 2023

Related U.S. Application Data

(63) Continuation of application No. 17/143,791, filed on Jan. 7, 2021, which is a continuation of application
(Continued)

(51) Int. Cl.
*A61B 34/20* (2016.01)
*A61B 46/10* (2016.01)
(Continued)

(52) U.S. Cl.
CPC .......... *A61B 34/20* (2016.02); *A61B 5/6847* (2013.01); *A61B 17/1703* (2013.01);
(Continued)

(58) Field of Classification Search
CPC ......... A61B 34/20; A61B 46/10; A61B 17/17; A61B 17/1703; A61B 5/68; A61B 5/6847; G06T 7/33; G06T 7/337
See application file for complete search history.

(56) References Cited

U.S. PATENT DOCUMENTS

| 6,285,902 B1 * | 9/2001 | Kienzle, III ....... A61B 17/1721 378/205 |
| 8,348,954 B2 | 1/2013 | Carls et al. |
(Continued)

FOREIGN PATENT DOCUMENTS

| WO | 2006075331 A2 | 7/2006 |
| WO | 2006128301 A1 | 12/2006 |

OTHER PUBLICATIONS

International Search Report dated Feb. 5, 2016 for Related International PCT Patent Application No. PCT/CA2015/000558.
(Continued)

*Primary Examiner* — Christopher J Beccia

(57) ABSTRACT

Systems and methods are disclosed for use in electronic guidance systems for surgical navigation. A sensor is provided with an optical sensor, to provide optical information, and a measuring sensor, to provide measurements for determining a direction of gravity. The sensor communicates optical information and measurements to an inter-operative computing unit. In an embodiment, the inter-operative computing unit receives first optical information for a registration device and a patient anatomy and a measurement to determine a direction of gravity to perform a registration step. The inter-operative computing unit receives second optical information for the patient anatomy and an object and determines and presents measurements relative to the anatomy. The measurements relative to the anatomy are
(Continued)

determined from the second optical information, and in relation to the registration of the anatomy of the patient.

20 Claims, 24 Drawing Sheets

Related U.S. Application Data

No. 16/871,982, filed on May 11, 2020, now Pat. No. 10,898,278, which is a continuation of application No. 16/036,182, filed on Jul. 16, 2018, now Pat. No. 10,786,312, which is a continuation of application No. 15/656,347, filed on Jul. 21, 2017, now Pat. No. 10,034,715, which is a continuation of application No. 15/425,690, filed on Feb. 6, 2017, now Pat. No. 9,713,506, which is a continuation-in-part of application No. 15/148,084, filed on May 6, 2016, now Pat. No. 9,603,671, which is a continuation of application No. PCT/CA2015/000558, filed on Oct. 29, 2015.

(60) Provisional application No. 62/072,041, filed on Oct. 29, 2014, provisional application No. 62/072,030, filed on Oct. 29, 2014, provisional application No. 62/084,891, filed on Nov. 26, 2014, provisional application No. 62/072,032, filed on Oct. 29, 2014.

(51) Int. Cl.
| | |
|---|---|
| *A61B 5/00* | (2006.01) |
| *A61B 90/30* | (2016.01) |
| *A61B 90/00* | (2016.01) |
| *A61B 17/17* | (2006.01) |
| *A61B 34/10* | (2016.01) |
| *G06T 7/73* | (2017.01) |
| *G06T 7/33* | (2017.01) |

(52) U.S. Cl.
CPC .............. *A61B 34/10* (2016.02); *A61B 46/10* (2016.02); *A61B 90/06* (2016.02); *A61B 90/30* (2016.02); *A61B 90/361* (2016.02); *G06T 7/337* (2017.01); *G06T 7/74* (2017.01); *A61B 2034/105* (2016.02); *A61B 2034/2048* (2016.02); *A61B 2034/2055* (2016.02); *A61B 2034/2057* (2016.02); *A61B 2034/2065* (2016.02); *A61B 2034/2068* (2016.02); *A61B 2034/2072* (2016.02); *A61B 2090/061* (2016.02); *A61B 2090/064* (2016.02); *A61B 2090/067* (2016.02); *A61B 2090/364* (2016.02); *A61B 2090/373* (2016.02); *A61B 2090/3937* (2016.02); *A61B 2090/3983* (2016.02); *G06T 2207/30008* (2013.01)

(56) References Cited

U.S. PATENT DOCUMENTS

| | | | |
|---|---|---|---|
| 8,675,939 B2 | 3/2014 | Moctezuma De La Barrera | |
| 9,603,671 B2 | 3/2017 | Hladio et al. | |
| 9,713,506 B2 | 7/2017 | Fanson et al. | |
| 10,034,715 B2* | 7/2018 | Fanson | A61B 5/6847 |
| 10,898,278 B2* | 1/2021 | Fanson | A61B 34/10 |
| 2006/0190011 A1* | 8/2006 | Ries | A61B 90/36 |
| | | | 606/1 |
| 2010/0069919 A1 | 3/2010 | Carls et al. | |

OTHER PUBLICATIONS

Written Opinion dated Feb. 5, 2016 for Related International PCT Patent Application No. PCT/CA2015/000558.

* cited by examiner

| Difference from captured registration | |
|---|---|
| Pitch | +1° |
| Roll | -5° |
| Yaw | +0° |

1602
Axis frame device is brought into partial alignment with a patient's pelvis, i.e. in atleast one degree of freedom in orientation

1604
Once frame is in alignment, sensor captures position and/or orientation of axis frame

1606
While the patient is positioned laterally, an inclination measurement is captured

1608
Computing unit computes registration based on the position and/or orientation of axis frame and inclination measurements

Figure 16

1702
Probe device is used to localize atleast two landmarks along the frontal plane of the pelvis 1704
Sensor captures location of landmarks 1706
While the patient is positioned laterally, an inclination measurement is captured 1708
Computing unit computes registration based on the position and/or orientation of probe and inclination measurements

1801
Measure a direction of gravity using a sensor, sensor comprising optical sensor and inclinometer, attached to patient anatomy in known orientation with respect to gravity

1802
Measure a direction of an axis of a device, device having a shape defining at least one axis using positional information in up to 6DOF provided by a target to the optical sensor, and known positional relationship between target and device

1803
Construct a registration coordinate frame to register anatomy during surgery based on direction of gravity, direction of axis, and known orientation of patient with respect to gravity

2001
Receiving medical image data of anatomy of patient, where the medical image data is generated from medical images, such medical images made when the patient was in a first known orientation with respect to an arbitrary plane, the medical image data having properties defining a second known orientation of imaging equipment with respect to the arbitrary plane, a direction of an identifiable anatomical axis of the anatomy and a location of an identifiable anatomical point of the anatomy 2002
Measuring a direction of at least one axis of the anatomy with respect to a reference element, the reference element attached to the patient and the patient in the first known orientation with respect to an arbitrary plane, using optical measurements from a sensor comprising an optical sensor and a target attached to a first registration device, the first registration device having a known positional relationship with the target, and the target configured to provide positional information in up to 6 DOF, the direction of the axis coinciding with the direction of the identifiable anatomical axis of the medical image data 2003
Measuring an orientation of the arbitrary plane with respect to the reference element using optical measurements from the optical sensor generated with the target attached to a plane registration device, the plane registration device having a known positional relationship with the target 2004
Determining a computed location of at least one point of the anatomy with respect to the reference element using optical measurements from the optical sensor generated with the target attached to a second registration device, the at least one point coinciding with the identifiable anatomical point of the anatomy in the medical image data

Figure 20A

2005
Constructing a registration coordinate frame to register the anatomy of the patient with respect to the reference element using the orientation of the arbitrary plane and the direction of the axis of the anatomy

2006
Constructing an image registration coordinate frame to register the anatomy of the patient to the medical image data using the direction of the identifiable anatomical axis, the direction of the at least one axis of the anatomy, the location of the identifiable anatomical point of the anatomy, the computed location of at least one point of the anatomy, the orientation of the arbitrary plane, and the second known orientation with respect to the arbitrary plane

2007
Providing surgical measurements with respect to the medical image data to a display unit in a surgical procedure based on the registration coordinate frame and the image registration coordinate frame

2111
Receiving medical image data of anatomy of patient, where the medical image data is generated from medical images, such medical images made when the patient was in a first known orientation with respect to an arbitrary plane, the arbitrary plane is perpendicular to gravity, the medical image data having properties defining a second known orientation of imaging equipment with respect to the arbitrary plane, a direction of an identifiable anatomical axis of the anatomy and a location of an identifiable anatomical point of the anatomy

2112
Measuring a direction of at least one axis of the anatomy with respect to a reference element, the reference element attached to the patient and the patient in the first known orientation with respect to the arbitrary plane, using optical measurements from a sensor comprising an optical sensor and a target attached to a first registration device, the first registration device having a known positional relationship with the target, and the target configured to provide positional information in up to 6 DOF, the direction of the axis coinciding with the direction of the identifiable anatomical axis of the medical image data

2113
Measuring an orientation of the arbitrary plane with respect to the reference element comprises using inclination measurements from the sensor to measure a direction of gravity, the sensor further comprising an inclinometer

2114
Determining a computed location of at least one point of the anatomy with respect to the reference element using optical measurements from the optical sensor generated with the target attached to a second registration device, the at least one point coinciding with the identifiable anatomical point of the anatomy in the medical image data

Figure 21A

2115
Constructing a registration coordinate frame to register the anatomy of the patient with respect to the reference element using the orientation of the arbitrary plane and the direction of the axis of the anatomy

2116
Constructing an image registration coordinate frame to register the anatomy of the patient to the medical image data using the direction of the identifiable anatomical axis, the direction of the at least one axis of the anatomy, the location of the identifiable anatomical point of the anatomy, the computed location of at least one point of the anatomy, the orientation of the arbitrary plane, and the second known orientation with respect to the arbitrary plane

2117
Providing surgical measurements with respect to the medical image data to a display unit in a surgical procedure based on the registration coordinate frame and the image registration coordinate frame

2301
Obtaining target parameters for a surgical procedure using medical image data of an anatomy of a patient, the patient positioned in a first known orientation with respect to an arbitrary plane, the target parameters having a known relationship to the arbitrary plane and to an identifiable anatomical direction of the anatomy of the patient 2302
Invoking an electronic guidance system to capture a direction of an intra-operative axis of the anatomy of the patient using a sensor of the electronic guidance system, the patient positioned in the first known orientation with respect to the arbitrary plane, and the direction of the intra-operative axis coinciding with the identifiable anatomical direction 2303
Invoking the electronic guidance system to capture an orientation of an intra-operative plane of the anatomy of the patient using the sensor, the orientation of the intra-operative plane coinciding with an arbitrary plane 2304
Viewing surgical measurements provided by the electronic guidance system with respect to the intra-operative plane and the intra-operative axis of the anatomy of the patient; and 2305
Performing the surgical procedure while comparing the surgical measurements and the target parameters.

2311
Obtaining target parameters for a surgical procedure using medical image data of an anatomy of a patient, the patient positioned in a first known orientation with respect to an arbitrary plane, the target parameters having a known relationship to the arbitrary plane and to an identifiable anatomical direction of the anatomy of the patient

2312
Loading medical image data and optionally, target parameters, into an intra-operative computing unit of an electonic guidance system

2313
Invoking the electronic guidance system to capture optical measurements and optionally, inclination measurements, to register the anatomy of the patient

2314
Viewing surgical measurements provided by the electronic guidance system with respect to an intra-operative plane and an intra-operative axis of the anatomy of the patient and using the surgical measurements to achieve the target parameters, if provided

Figure 23B

SYSTEMS AND METHODS TO REGISTER PATIENT ANATOMY OR TO DETERMINE AND PRESENT MEASUREMENTS RELATIVE TO PATIENT ANATOMY

CROSS-REFERENCE TO RELATED APPLICATIONS

This application is a continuation of U.S. Ser. No. 17/143,791 titled "Systems, Methods And Devices To Measure And Display Inclination And Track Patient Motion During A Procedure" and filed Jan. 7, 2021 (the "'791 application"). The '791 application is a continuation of U.S. Ser. No. 16/871,982 titled "Systems, Methods And Devices To Measure And Display inclination And Track Patient Motion During A Procedure" and filed May 11, 2020, which is a continuation of U.S. application Ser. No. 16/036,182 titled "Systems, Methods and Devices to Measure and Display Inclination and Track Patient Motion During a Procedure" and filed Jul. 16, 2018, which is a continuation of U.S. application Ser. No. 15/656,347 titled "Systems, Methods and Devices to Measure and Display Inclination and Track Patient Motion During a Procedure" and filed on Jul. 21, 2017, which is a continuation of U.S. application Ser. No. 15/425,690 titled "Systems, methods and devices for image registration and surgical localization" and filed on Feb. 6, 2017, which is a continuation-in-part of U.S. application Ser. No. 15/148,084 titled "Systems, methods and devices for anatomical registration and surgical localization" and filed on May 6, 2016, which is a 35 U.S.C. 111(a) application of PCT application no. PCT/CA2015/000558 filed on Oct. 29, 2015, which claims priority to U.S. provisional application No. 62/072,041 titled "Systems, Methods and Devices for Anatomical Registration and Surgical Localization" and filed on Oct. 29, 2014, U.S. provisional application No. 62/072,030 titled "Devices including a surgical navigation camera and systems and methods for surgical navigation" and filed on Oct. 29, 2014, U.S. provisional application No. 62/084,891 titled "Devices, systems and methods for natural feature tracking of surgical tools and other objects" and filed on Nov. 26, 2014, U.S. provisional application No. 62/072,032 titled "Devices, systems and methods for reamer guidance and cup seating" and filed on Oct. 29, 2014. The entire contents of all applications listed above are incorporated herein by reference.

FIELD

The present specification relates to systems and methods register patient anatomy or to determine and present measurements relative to patient anatomy.

BACKGROUND

A human hip joint is a ball and socket joint comprising the head of a femur bone (femoral head) located in an acetabulum of a human pelvis. During total hip arthroplasty (THA), the hip joint of a patient is replaced with prosthetic components. The surgical procedure involves the surgical excision of the head and proximal neck of the femur bone and removal of the acetabular cartilage and subchondral bone. An artificial canal is created in the proximal medullary region of the femur, and a metal femoral prosthesis is inserted into the femoral medullary canal. An acetabular component or implant is inserted proximally in the enlarged acetabular space.

One of the most important aspects of THA is ensuring proper alignment of the acetabular component or implant with respect to the pelvis. Alignment of the prosthetic components has typically been performed relying solely on a surgeon's judgment of the spatial location of the prosthetic components. Studies have shown that failure to properly align the acetabular component or implant with the pelvis may lead to premature wear, propensity to dislocate and patient discomfort. Surgical navigation systems can assist surgeons in providing guidance in the placement of the prosthesis in the body of the patient to improve clinical outcomes. A surgeon may obtain a pre-operative scan providing medical images of the patient's anatomy of interest. During the surgical procedure, systems may provide intra-operative surgical navigation by providing surgical measurements with respect to the medical images.

BRIEF SUMMARY

This specification describes systems, methods and devices for use in electronic guidance systems for surgical navigation. A sensor is provided having an inclinometer (e.g. accelerometer or other inclination measuring sensor) and communicates measurements of patient inclination to an inter-operative computing unit. The sensor may also have an optical sensor. The computing unit is configured to determine patient movement (e.g. relative to an initial patient position) and provide inclination measurements graphically via a Graphical User Interface (GUI) to represent patient movement during a procedure. The graphic may be selectively displayed. In one example, a bubble level graphic is displayed to indicate patient movement. A direction of the bubble level may utilize a registration coordinate frame of the patient and the current inclination expressed with respect to the anatomical directions of the patient.

This specification also describes methods, systems and devices used to register the body of the patient to an electronic guidance system for surgical navigation. During surgery guided by electronic navigation, a surgeon typically has to determine a correlation between the coordinate reference frame of a patient and that of the electronic guidance system for surgical navigation. This allows the surgeon to use his/her clinical judgment when viewing the measurements and deciding the final placement of objects, such as a hip prosthesis, in the body of the patient. The surgical navigation system needs to know the correlation so that measurements can be provided in one or both coordinate frames.

Further, if there is a desire to perform image-guided surgical navigation i.e. surgical measurements calculated and displayed with respect to the patient's medical images, the system may obtain pre-operative scans of the patient's anatomy comprising medical images, each image having an image coordinate frame. The image coordinate frame can be correlated to a coordinate frame of the patient's anatomy during the surgical procedure (in a process called "image registration") and subsequent surgical measurements may be provided accordingly. The term "pre-operative" suggests that the scans are obtained prior to the beginning of a surgical procedure—a few hours to a few days earlier. However, this term as used in this specification also intends to cover intra-operative scans that utilize imaging equipment placed inside a surgical theatre and are used to obtain information about the patient's anatomy during a surgical procedure. The imaging equipment may be the same regardless of when and where the scan is captured.

There is disclosed a system to provide intra-operative surgical navigation with respect to medical image data. The system comprises a sensor comprising an optical sensor to generate optical measurements; a target configured to provide positional information to the optical sensor, the optical sensor generating the optical measurements using the positional information in up to six degrees of freedom; a reference element configured to attach to an anatomy of a patient, the patient positioned in a first known orientation with respect to an arbitrary plane; a first registration device attached to the target, the first registration device having a known positional relationship with the target; and an intra-operative computing unit in communication with the sensor, the intra-operative computing unit configured to receive medical image data of the anatomy of the patient, the medical image data generated from medical images obtained when the anatomy of the patient was in the first known orientation with respect to the arbitrary plane and having properties defining a second known orientation of an imaging equipment with respect to the arbitrary plane, a direction of an identifiable anatomical axis of the anatomy of the patient and a location of an identifiable anatomical point of the anatomy of the patient; measure a direction of at least one axis of the anatomy of the patient with respect to the reference element using optical measurements from the optical sensor generated with the target attached to the first registration device, the direction of the axis coinciding with the direction of the identifiable anatomical axis of the medical image data; determine a computed location of at least one point of the anatomy of the patient with respect to the reference element using optical measurements from the optical sensor generated with the target attached to a second registration device, the second registration device having a known positional relationship with the target, and the location of the at least one point coinciding with the location of the identifiable anatomical point of the anatomy of the patient in the medical image data; measure an orientation of the arbitrary plane with respect to the reference element using the sensor; construct a registration coordinate frame to register the anatomy of the patient with respect to the reference element using the orientation of the arbitrary plane and the direction of the axis of the anatomy of the patient; construct an image registration coordinate frame to register the anatomy of the patient to the medical image data using the direction of the identifiable anatomical axis, the direction of the at least one axis of the anatomy of the patient, the computed location of the at least one point of the anatomy, the location of the identifiable anatomical point of the anatomy, the orientation of the arbitrary plane, and the second known orientation of the imaging equipment with respect to the arbitrary plane; and provide surgical measurements with respect to the medical image data to a display unit in a surgical procedure based on the registration coordinate frame and the image registration coordinate frame. The first registration device and the second registration device may be a single registration device. The single registration device may be removably attached to the target. The first registration device and the second registration device may be one of a probe, an alignment rod and a flat surface plate.

The intra-operative computing unit may measure the orientation of the arbitrary plane using optical measurements from the optical sensor generated with the target attached to a plane registration device, the plane registration device having a known positional relationship with the target. The first registration device, the second registration device and the plane registration device may be a single registration device. The first registration device, the second registration device and the plane registration device may be one of a probe, an alignment rod and a flat surface plate. The reference element may be the optical sensor. The sensor may further comprise an inclinometer to generate inclination measurements, the arbitrary plane may be perpendicular to gravity and the intra-operative computing unit may measure the orientation of the arbitrary plane by measuring a direction of gravity with respect to the reference element using the inclination measurements from the inclinometer. The sensor may be configured to generate optical measurements and inclination measurements relative to a common frame of reference using a rigid mechanical relationship between the optical sensor and the inclinometer. The intra-operative computing unit may be further configured to provide surgical measurements using optical measurements from the optical sensor generated with the target attached to a surgical tool. The surgical procedure may be a Total Hip Arthroplasty and the anatomy of the patient may be a pelvis. The surgical tool may be an acetabular cup impactor. The intra-operative computing unit may be further configured to receive medical image data of the anatomy of the patient with the medical image data further having properties defining an identifiable location of additional anatomical features of the anatomy of the patient; determine a computed location of additional anatomical features of the patient using optical measurements of the optical sensor generated with the target attached to one of the first registration device and second registration device; construct a fine registration coordinate frame and a fine image registration coordinate frame using the computed location of additional anatomical features and the identifiable location of additional anatomical features; and provide surgical measurements with respect to the medical image data to a display unit in a surgical procedure based on the fine registration coordinate frame and the fine image registration coordinate frame.

There is disclosed a computer-implemented method comprising receiving, by at least one processing unit, medical image data of an anatomy of a patient, the medical image data generated from medical images obtained when the anatomy of the patient was in a first known orientation with respect to an arbitrary plane, the anatomy having a reference element configured to attach to it and the patient positioned in the first known orientation with respect to the arbitrary plane, the medical image data further having properties defining a second known orientation of an imaging equipment with respect to the arbitrary plane, a direction of an identifiable anatomical axis of the anatomy of the patient and a location of an identifiable anatomical point of the anatomy of the patient; measuring, by at least one processing unit, a direction of at least one axis of the anatomy of the patient with respect to the reference element using optical measurements from a sensor comprising an optical sensor, and a target attached to a first registration device, the first registration device having a known positional relationship with the target, and the target configured to provide positional information to the optical sensor, the optical sensor generating optical measurements using the positional information in up to six degrees of freedom, the direction of the axis coinciding with the direction of the identifiable anatomical axis of the medical image data; measuring, by at least one processing unit, an orientation of the arbitrary plane with respect to the reference element using the sensor; determining, by at least one processing unit, a computed location of at least one point of the anatomy of the patient with respect to the reference element using optical measurements from the optical sensor generated with the target attached to a second registration device, the computed location of the at least one point coinciding with the location of the identifiable anatomical point of the anatomy of the patient in the medical image data; constructing, by at least one processing unit, a registration coordinate frame to register the anatomy of the patient with respect to the reference element using the orientation of the arbitrary plane and the direction of the axis of the anatomy of the patient; constructing, by at least one processing unit, an image registration coordinate frame to register the anatomy of the patient to the medical image data using the direction of the identifiable anatomical axis, the direction of the axis of the anatomy of the patient, the location of the identifiable anatomical point of the anatomy, the computed location of at least one point of the anatomy of the patient, the orientation of the arbitrary plane, and the second known orientation with respect to the arbitrary plane; and providing, by at least one processing unit, surgical measurements with respect to the medical image data to a display unit in a surgical procedure based on the registration coordinate frame and the image registration coordinate frame. The step of measuring, by the at least one processing unit, the orientation of the arbitrary plane with respect to the reference element may comprise using optical measurements from the optical sensor generated with the target attached to a plane registration device, the plane registration device having a known positional relationship with the target. The arbitrary plane may be perpendicular to gravity and the step of measuring, by at least one processing unit, a direction of gravity may comprise using inclination measurements from the sensor, the sensor further comprising an inclinometer.

The method may further comprise the step of providing, by at least one processing unit, image-guided surgical navigation using optical measurements from the optical sensor generated with the target attached to a surgical tool. The surgical tool may be an acetabular cup impactor. The reference element may be the optical sensor.

There is disclosed a system to provide intra-operative guidance during THA. The system comprises: a sensor configured to attach to an anatomy of a patient, positioned in a known orientation with respect to gravity, and comprising an optical sensor to generate optical measurements and an inclinometer to generate inclination measurements; a target configured to provide positional information to the optical sensor, the optical sensor generating the optical measurements using the positional information in up to six degrees of freedom; a device attached to the target, the device having a shape defining at least one axis, wherein the at least one axis is in a known positional relationship with the target; and an intra-operative computing unit in communication with the sensor. The intra-operative computing unit is configured to: measure a direction of at least one axis using the optical measurements from the sensor and the known positional relationship between the target and the device; measure a direction of gravity based on the inclination measurements; and construct a registration coordinate frame to register the anatomy of the patient during surgery to provide surgical navigation based on the direction of gravity, the direction of the axis and the known orientation of the patient with respect to gravity. The intra-operative computing unit is further configured to calculate, in real-time, a difference in the optical measurements in at least one degree of freedom provided by the optical sensor with respect to the registration coordinate frame and to provide the difference for display by a display unit. A sensor configured to attach to an anatomy of a patient, the anatomy being a pelvis. The device may be removably attached to the target.

There is disclosed a medical navigational guidance system wherein the intra-operative computing unit is further configured to construct the common frame of reference using a rigid mechanical relationship between the optical sensor and the inclinometer. The intraoperative computing unit is further configured to construct the registration coordinate frame using redundant measurement information wherein the redundant measurement information is used to compute a metric representing the consistency between the inclination measurements and optical measurements received from the sensor; and provide the metric to a display unit for displaying to a surgeon. The sensor is configured to generate optical measurements and inclination measurements relative to a common frame of reference.

There is disclosed a system for providing navigational guidance during THA. The system comprises: a sensor configured to attach to an anatomy of a patient, comprising an optical sensor to generate optical measurements and an inclinometer configured to generate inclination measurements; a target configured to provide positional information to the optical sensor, the optical sensor generating the optical measurements using the positional information in up to six degrees of freedom; a probe attached to the target, the probe having a tip, wherein the tip is in a known positional relationship with the target; and an intra-operative computing unit in communication with the sensor. The intra-operative computing unit is configured to: determine a location of two or more anatomical features of the patient, the features lying on the anterior pelvic plane of the patient, using optical measurements of the sensor and the known positional relationship between the target and the tip of the probe; calculate a direction of at least one axis defined by the location of the two or more anatomical features; and construct a registration coordinate frame to register, during surgery, the anatomy of the patient based on the direction of gravity and the direction of the axis. The intra-operative computing unit is further configured to generate a secondary registration coordinate frame by localizing three anatomical features on the acetabular rim of the patient. The system is configured to provide navigational guidance based on the registration coordinate frame and the secondary registration coordinate frame. A sensor configured to attach to an anatomy of a patient, the anatomy being a pelvis. The probe may be removably attached to the target.

There is disclosed a computer-implemented method for a medical navigation guidance system capable of: measuring, by at least one processing unit, a direction of gravity using a sensor, the sensor comprising an optical sensor and an inclinometer, attached to an anatomy of a patient positioned in a known orientation with respect to gravity; measuring, by at least one processing unit, a direction of an axis of a device, the device having a shape defining at least one axis using positional information in up to six degrees of freedom provided by a target to the optical sensor, and a known positional relationship between the target and the device; and constructing, by at least one processing unit, a registration coordinate frame to register, during surgery, the anatomy of the patient based on the direction of gravity, the direction of the axis and the known orientation of the patient with respect to gravity. When the patient is positioned in a second orientation, the intra-operative computing unit is further configured to provide surgical navigation based on the registration coordinate frame.

There is disclosed a medical navigational guidance system comprising: a sensor comprising an optical sensor configured to generate optical measurements and an inclinometer configured to generate inclination measurements; a first target attached to an anatomy of a patient configured to provide positional signals in up to six degrees of freedom to the optical sensor; a second target configured to provide positional information in up to six degrees of freedom to the optical sensor and configured to be attached to a device with a shape that defines at least one axis, wherein the at least one axis has a known positional relationship with the second target; and an intra-operative computing unit. The sensor is configured to attach to an operating table. The sensor is further configured to be held in the hand of a surgeon. The intra-operative computing unit is configured to: receive positional signals of the first target from the optical sensor; receive inclination measurements from the inclinometer; calculate position and orientation of the first target; calculate the direction of gravity with respect to the position and orientation of the first target based on the inclination measurements; measure the direction of the at least one axis using positional information provided by the second target and the known positional relationship between the second target and the device; and construct a registration coordinate frame for the anatomy of the patient based on the direction of gravity with respect to the first target, position and orientation of the first target and the direction of the axis.

BRIEF DESCRIPTION OF DRAWINGS

Embodiments disclosed herein will be more fully understood from the detailed description and the corresponding drawings, which form a part of this specification, and in which:

FIG. 6 is a screenshot of a representative verification feature in a display unit of a workstation of the electronic guidance system in accordance with an embodiment;

FIG. 16 is a flowchart of a method for registration using an axis frame and inclination measurements in accordance with an embodiment;

FIG. 17 is a flowchart of a method for registration using inclination measurements and localized landmarks in accordance with an embodiment; and FIG. 18 is a flowchart of a computer-implemented method for registration using an axis frame and inclination measurements.

FIGS. 20A and 20B together are a flowchart of a computer implemented method for image registration using optical measurements from an optical sensor;

FIGS. 21A and 21B together are a flowchart of a computer implemented method for image registration using optical measurements from an optical sensor and inclination measurements from an inclinometer;

FIGS. 23A and 23B are flowcharts of methods of use to register the patient's anatomy to medical image data and use of the electronic guidance system for intra-operative navigation.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

Systems, methods and devices are presented herein pertaining to anatomical registration and surgical localization during surgical navigation. The embodiments refer to use of an electronic guidance system in THA. However, a person skilled in the art will realize that the specification is applicable to other forms of surgery and is not meant to be limited to THA. It is further understood that various methods described for performance by a computer system such as navigational surgery may be implemented in software such as instructions and data to configure at least one processing unit of a computer system to perform the method. The instructions and data may be stored in a device such as a memory (RAM, ROM, flash drive, etc.) or other non-transitory storage device (e.g.: magnetic, optical, or other disk or storage medium).

Several systems, methods and devices will be described below as embodiments. The scope of the claims should not be limited by the embodiments set forth in the examples, but should be given the broadest interpretation consistent with the description as a whole.

Figure 1:
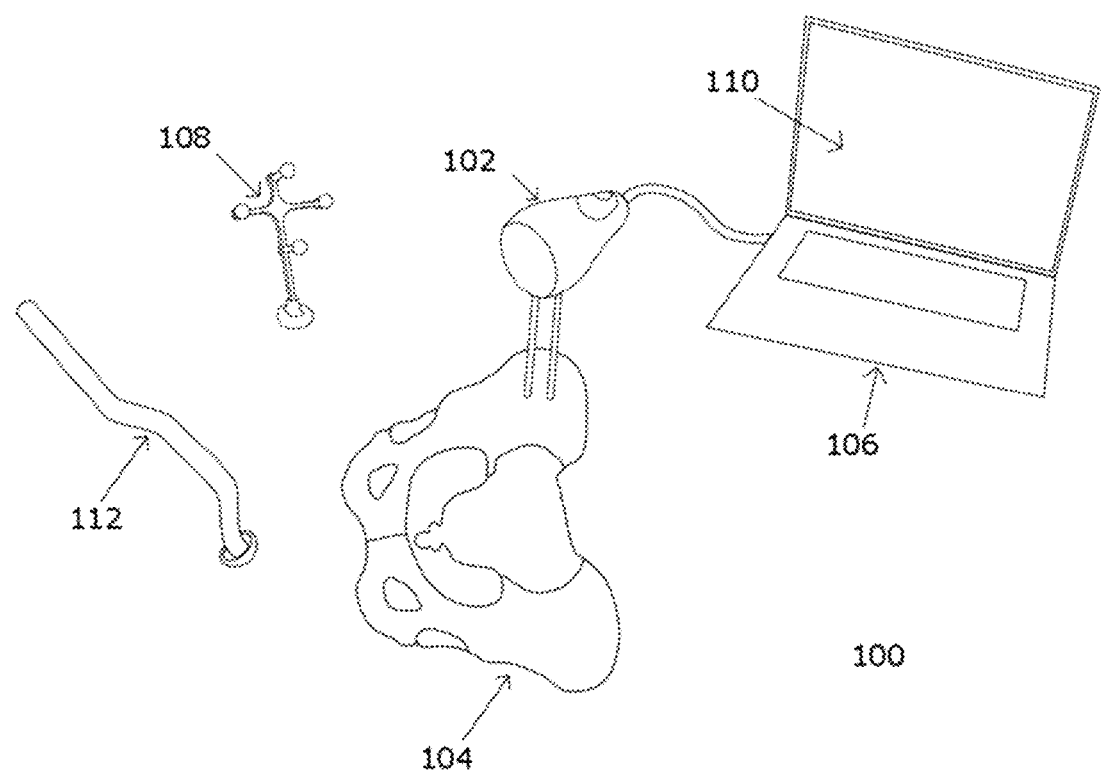
FIG. 1 shows some components of an electronic guidance system in accordance with an embodiment.

In order to provide electronic guidance with respect to the anatomy of the patient in THA, the spatial coordinates of the anatomy of the patient (e.g., the pelvis) with respect to the electronic guidance system are required. This step is referred to as "registration" in this specification. Further, if image-guided surgical navigation is to be provided with respect to one or more medical images of the anatomy of the patient, then the spatial coordinates of the anatomy of the patient are correlated to the spatial coordinates of the anatomy as it appears on one or more medical images. This step is referred to as "image registration" in this specification. Anatomical registration pertains to generating a digital positional or coordinate mapping between the anatomy of interest and a localization system or an electronic guidance system. Similarly, image registration generates a digital positional or coordinate mapping between the anatomy of interest and one or medical images that were captured during a pre-operative scan of the anatomy. There are multiple methods to obtain this registration mapping or the registration coordinate frame between the anatomy and the system. There are also multiple methods to obtain the registration mapping or image registration coordinate frame between the anatomy and one or more medical images. It is desirable that these methods of registration are fast, so as to not increase the duration of the surgical workflow, and sufficiently accurate. The electronic guidance system can utilize the registration coordinate frame or the image registration coordinate frame to intra-operatively provide clinically relevant measurements to the surgeon using the system. FIG. 1 illustrates an electronic guidance system 100 used in THA where a sensor 102 is attached an anatomy of a patient (e.g. a pelvis 104) and communicates with a workstation or an intra-operative computing unit 106. The pose (position and orientation) of a target 108 can be detected by the sensor 102 and displayed on a graphical user interface (GUI) 110 of the workstation 106. The target 108 may be attached to an instrument 112 or to another part of the anatomy of the patient (e.g. to a femur). Surgical measurements for a THA may include one or more of the following—leg length, offset, anteversion, inclination etc. Medical image data comprises one or more raw medical images from the pre-operative scan or one or more digitally processed medical images by creating 3D surface models of anatomy represented by 3D point clouds or by using techniques of image segmentation, etc. The medical image data may be displayed on the GUI 110 of the workstation 106. Construction of an image registration coordinate frame allows the surgical measurements to be displayed with respect to the medical image data.

The medical images may be used in the original format (e.g. DICOM files) or may be pre-processed using image segmentation and other known methods of processing medical images to create medical image data that can be used for image-guided surgical navigation. The medical images may also have been obtained with the patient standing upright, lying supine or perhaps at an orientation to the imaging equipment. If the orientation of the images with respect to an arbitrary plane is provided, the workstation of the electronic guidance system can, along with other inputs, utilize this orientation information during image registration in the construction of the image registration coordinate frame.

Medical images are processed to create the medical image data and to have image properties that define a direction of an identifiable anatomical axis and a location of an identifiable anatomical point of the anatomy of the patient shown in the images. For example, the identifiable anatomical axis of the anatomy may be an axis extending along the superior-inferior direction of the anatomy or may be calculated by identifying two points that lie along the identifiable anatomical axis of the anatomy, and the identifiable anatomical point may be an ASIS on a pelvis of the patient, a center of rotation of a hip joint, etc. These image properties may be defined by the imaging equipment during the capture of the medical images by placing markers on the anatomy that appear on the medical images or may be identified by user input to a computing unit or other means while post-processing the medical images to create the medical image data. Intraoperatively, a corresponding axis and a corresponding anatomical point of the patient's anatomy are measured and determined by an intra-operative computing unit to construct the image registration coordinate frame.

The orientation of the arbitrary plane is also used to construct the registration coordinate frame and the image registration coordinate frame and it can be measured with respect to a reference element (described below) with the use of mechanical registration devices also described below. Pelvic registration, particularly useful in THA, is selected as an exemplary embodiment; however, this description is intended to be interpreted as applicable to general anatomy and in various other surgeries.

In this disclosure, normally a sensor is attached to a bone of the anatomy of the patient or a steady surface such as an operating table. A target, detectable by the sensor in up to six degrees of freedom, is located on an object being tracked, such as another bone of the anatomy of the patient, a tool, a prosthesis, etc. However, in general, the locations of the sensor and target can be reversed without compromising functionality (e.g. fixing the target on the bone or a steady surface and attaching the sensor to the object to be tracked), and this disclosure should be interpreted accordingly.

Furthermore, one skilled in the art will appreciate that the techniques, components, and methods described herein may be implemented using different tracking modalities. For example, use of traditional stereoscopic localization cameras (e.g. the Polaris™ product from Northern Digital Inc. in Waterloo, ON), electromagnetic tracking systems (e.g. the Aurora™ product from Northern Digital Inc), ultrasonic localizers (e.g. see U.S. Pat. No. 8,000,926), mechanical localization devices, RF localizers, etc. are contemplated.

Figure 12:
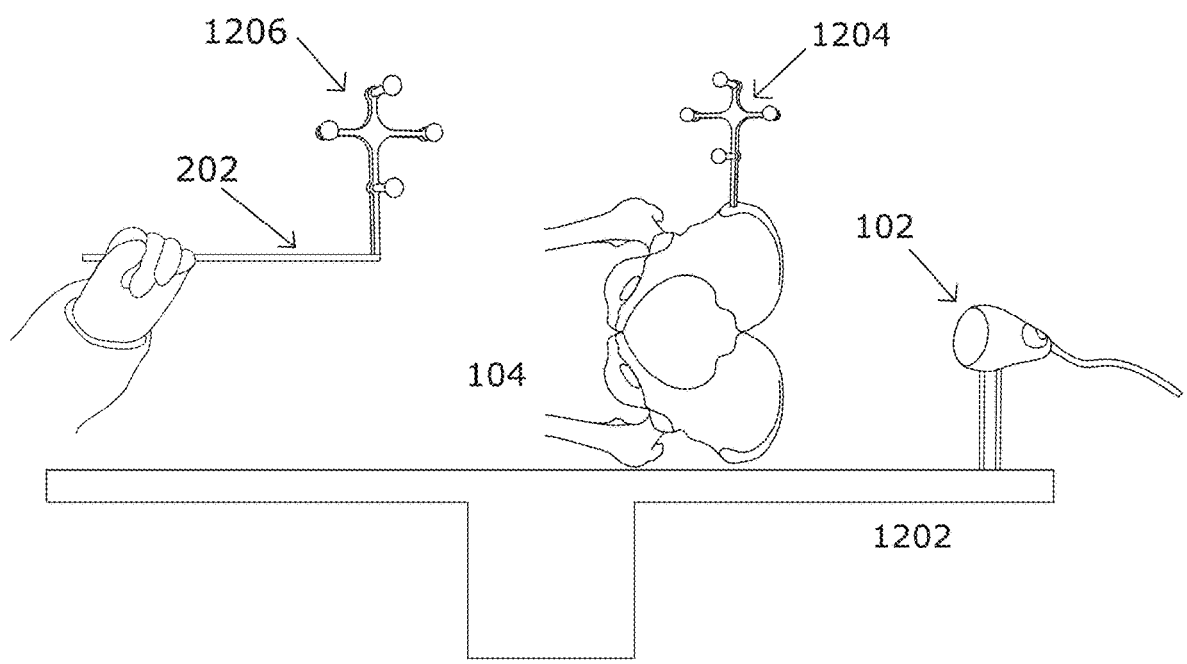
FIG. 12 shows an anatomy of a patient and a sensor attached to an operating table or bed to capture measurements from the axis frame as an example for clarity.

When the sensor is attached to the patient's anatomy, the reference element may be the sensor itself. All measurements calculated by the electronic guidance system may be and preferably are with respect to the sensor. FIG. 1 depicts a system in which the sensor is attached to the anatomy. When the sensor is attached to an operating table, a stand in the operating room or any other rigid location that is not on the patient, a reference element may be attached to the anatomy to allow the system to calculate the registration coordinate frame and other measurements with respect to the reference element. Optionally and without necessity, when the sensor is attached to the patient's anatomy a separate reference element may also be attached but such is not preferred. It may be identical to the target to be detectable by the optical sensor in up to six degrees of freedom or it may have a different spatial configuration of reflective elements that allow it to be tracked by the optical sensor. The reference element provides an alternate method of use of the electronic guidance system that allows the optical sensor to be positioned at a distance away from the anatomy of the patient, while the reference element is attached to the patient and is within a field of view of the optical sensor. FIG. 12, described further in the specification, depicts a system where the reference element is a target and the sensor is attached to the operating table.

Figure 2A:
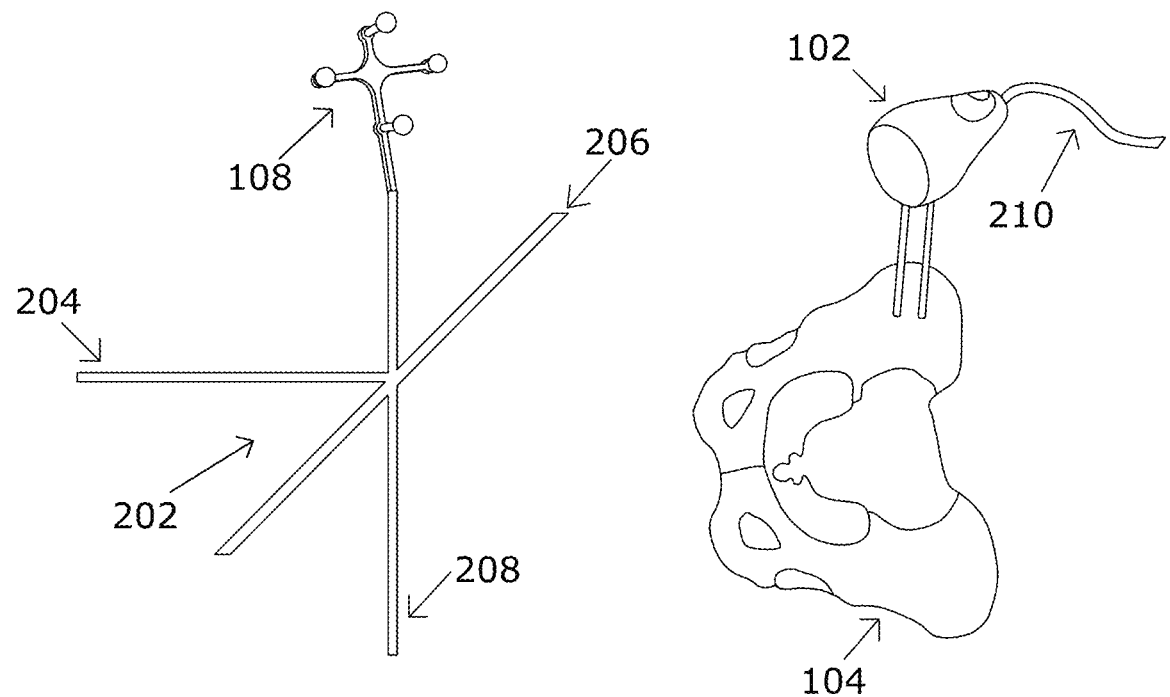
FIG. 2A shows a registration device (an axis frame) used in registration of a coordinate frame of a patient to that of the electronic guidance system for surgery in accordance with an embodiment.

Next, the present specification describes the use of mechanical registration devices in order to allow the system to generate the registration coordinate frame to map a patient's anatomy to the electronic guidance system and to generate the image registration coordinate frame to map the patient's anatomy to medical image data. The registration devices described herein include an axis frame with one or more axes, and a probe with a tip. These devices allow a target to be attached to it in a known positional relationship. Reference is now made to FIG. 2A, which illustrates a registration device 200, referred to as an axis frame 202 that may be used to register an anatomy of a patient to the electronic guidance system 100. Through its shape, an axis frame 202 can define axes, such as a first axis 204, a second axis 206 and a third 208 axis. For example, an axis frame may be comprised of three orthogonal bars (204, 206, and 208) that define three axes. The sensor 102 is attached to the pelvis of the anatomy 104 of the patient and communicates with an intra-operative computing unit 106 through a cable 210. The sensor may comprise an optical sensor to track positional information of the target 108 attached to the axis frame 202. This information is used to measure the directions of the anatomical axes of a patient in order to construct the registration coordinate frame. At the time of use, the positional relationship between the axes of the axis frame 202 and the target 108 must be known to the intra-operative computing unit 106, either through precise manufacturing tolerances, or via a calibration procedure. This relationship is vital to determining the registration coordinate frame. Generally, surgical grade metals are used to manufacture devices such as, an axis frame, as these metals are biocompatible and can be sterilized in a hospital setting.

Figure 3:
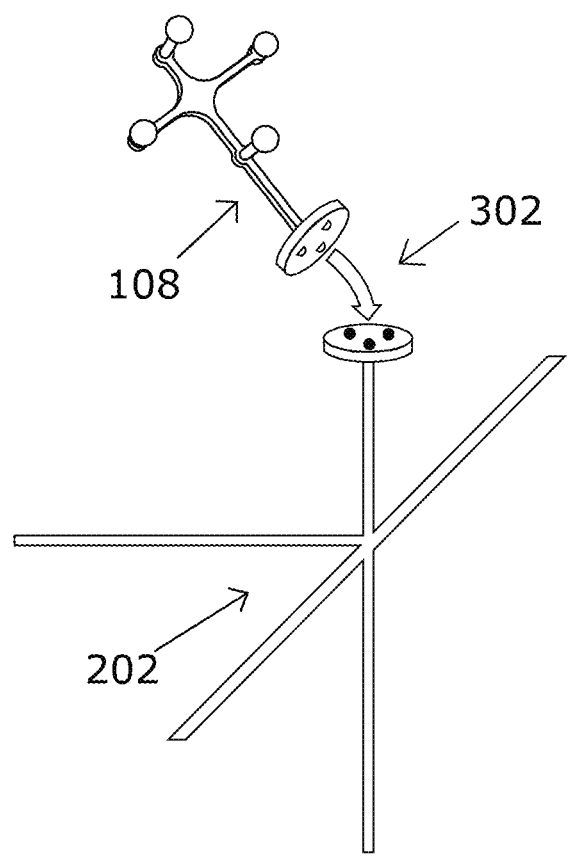
FIG. 3 shows a target member removably attached to an axis frame in accordance with an embodiment.

Rather than have a dedicated target for the axis frame, it may be advantageous to provide a removable target, such that the same target may be used to track a variety of instruments, implants and/or objects. The axis frame may have a target that is removably or integrally affixed to the axis frame and that can be tracked by the optical sensor. This is illustrated in FIG. 3, where the target 108 may be detached from the body of the axis frame 202, and may be coupled via a repeatable mount or quick connect mechanism 302, such as the one taught in U.S. 20140275940 titled "System and Method for Intra-Operative Leg Position Measurement" and filed on Mar. 15, 2013, the entire contents of which are incorporated herein by reference. The quick connect mechanism 302 is repeatable and accurate to ensure that the pose of the target 108 repeatably and accurately relates to the pose of the axis frame 202 in a pre-determined mathematical relation.

Figure 4:
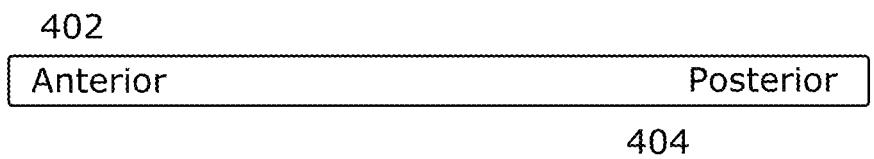
FIG. 4 shows labels on one of the axes of an axis frame as an example for clarity.

In addition to the shape of the axis frame that defines the axis/axes of interest for the purpose of registration, clinically relevant markings or labels may be used to define how the axis frame is intended to be aligned. In FIG. 4, for example, if a straight bar is used in an axis frame to define the anterior-posterior direction on a patient it may be labeled accordingly with an anterior label 402 and a posterior label 404.

An important aspect of the design of the axis frame is that it is trackable when in alignment with the anatomy. When the axis frame is aligned with the patient, the target must be within the field of view of the camera or sensor. This aspect may take into account patient-to-patient anatomical variations, as well as variations in the positioning of the sensor on the pelvis.

Figure 5:
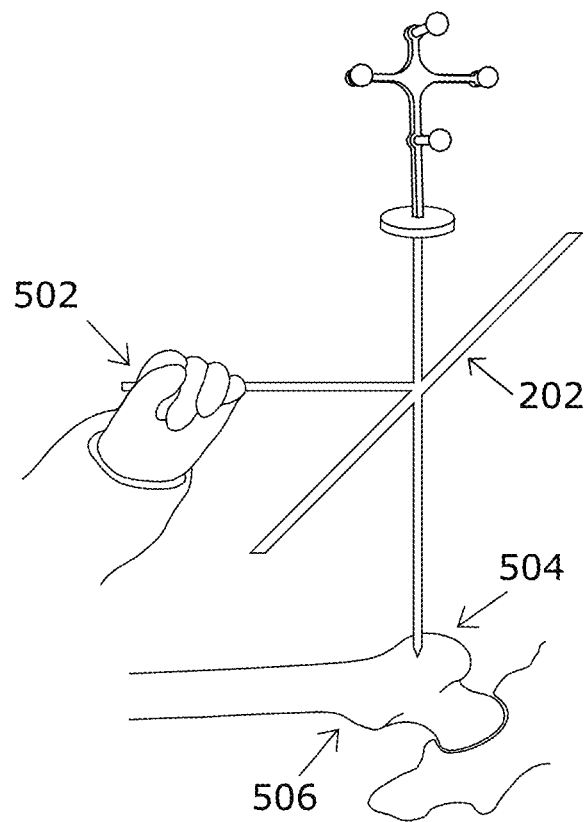
FIG. 5 shows the axis frame resting on a femur bone of a patient as an example for clarity.

Since the axis frame requires a user to manipulate it into the correct position with respect to the anatomy, ergonomic considerations for the user are important. In one embodiment as illustrated in FIG. 5, a hand 502 of a user is depicted holding an axis frame 202 with a contact point 504 resting on a femur 506 during a pelvic registration. A member comprising the contact point 504 may be at an additional attachment to the axis frame 202 such that it is attached only if and when required during the surgical workflow. The contact point 504 may be located at the tip of any of the axes of the axis frame 202. The purpose of the contact point 504 is to allow a user to manually rest the axis frame on a stable point such that the axis frame 202 is easier to manually align with the anatomy of interest. It is easier to align something when it is partially stabilized. The contact point 504 may be within a surgical wound, or outside. The location of the contact point 504 is not required to be repeatable.

A verification feature may be provided in the intra-operative computing unit. For example, after the registration coordinate frame has been calculated, the axis frame may continue to be tracked as it is manipulated by a user (e.g. a surgeon). As shown in FIG. 6, a GUI 110 on a display unit may update in real-time a current position of the axis frame relative to the registered position or coordinate frame. In this case, a metric, such as the three-dimensional difference in orientation, is depicted. Fewer degrees of freedom may also be depicted. This verification feature provides real-time feedback to the user, and allows the user to assess confidence in the positioning of the axis frame for registration. The computing unit may also allow the user to re-do the step of registration, should the user choose to do so. Although a numerical display is shown in FIG. 6, it may be preferable to include a graphical display, such as a bulls-eye graphic. The computing unit may provide guidance on how to move the axis frame in order to return to the original registered position.

Figure 2B:
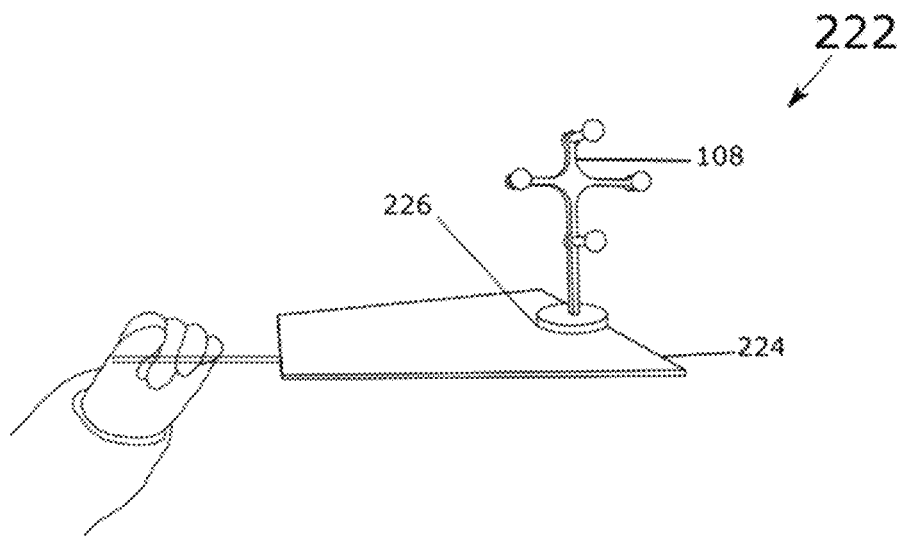
FIG. 2B shows a plane registration device as an example for clarity.

The verification feature also allows a user to verify and/or redo the registration steps at any point during the surgical procedure. It is preferable to perform the registration as soon as possible after the patient has been positioned and draped for surgery, such that the orientation of the anatomy (e.g. the pelvis) is known. The patient may then be moved (deliberately or unintentionally) as part of the surgical workflow without compromising the registration. Since the surgeon is typically involved in the preparation and draping, the surgeon will have a spatial awareness of the anatomical positioning of the patient with respect to the ground or to the operating table or to any other stationary object, even if the body of the patient is obscured by surgical draping. Furthermore, in many surgeries, the anatomy of the patient may shift or purposefully be moved as the surgeon may be required or may choose to position the patient into various positions. Registering the anatomical coordinate frame of the patient as soon as possible after patient positioning may eliminate patient shifting as a source of measurement error. Reference is now made to FIG. 2B that shows another example of a registration device 200—a plane registration device 222 with a flat, two-dimensional surface 224 and a location 226 to attach the target 108. The use of the plane registration device 222 and the target 108 allows the optical sensor to capture optical measurements to measure the arbitrary plane such that this arbitrary plane corresponds to an anatomical plane of the patient, for example, the coronal plane, the transverse plane, or the sagittal plane of the anatomy of the patient. At the time of use, the positional relationship between the flat surface 224 of the plane registration device 222 and the target 108 is known to the intra-operative computing unit 106, either through precise manufacturing tolerances, or via a calibration procedure. The plane registration device 222 provides sufficient information to the electronic guidance system to calculate up to two degrees of freedom of the anatomy of the patient. Preferably, the patient is lying supine and the arbitrary plane measured with the use of one of the registration devices corresponds to the horizontal plane (i.e. the plane orthogonal to gravity). The horizontal plane may also correspond to the supine coronal plane of the patient.

Another form of a registration device, for example a probe with a tip (not shown), may also be used to calculate the arbitrary plane. A plane can be defined mathematically with a known location of at least three points. By localizing three points on a surface (for example, an operating room table, the floor etc.) using the optical sensor and the target attached to the probe, the orientation of the arbitrary plane can be measured for use by the electronic guidance system in further calculations. Preferably, the surface is a sterile surface if the probe is used otherwise in a sterile field during the surgery.

The additional features of the axis frame described above are applicable to the structure and use of the plane registration device described herein.

Figure 7:
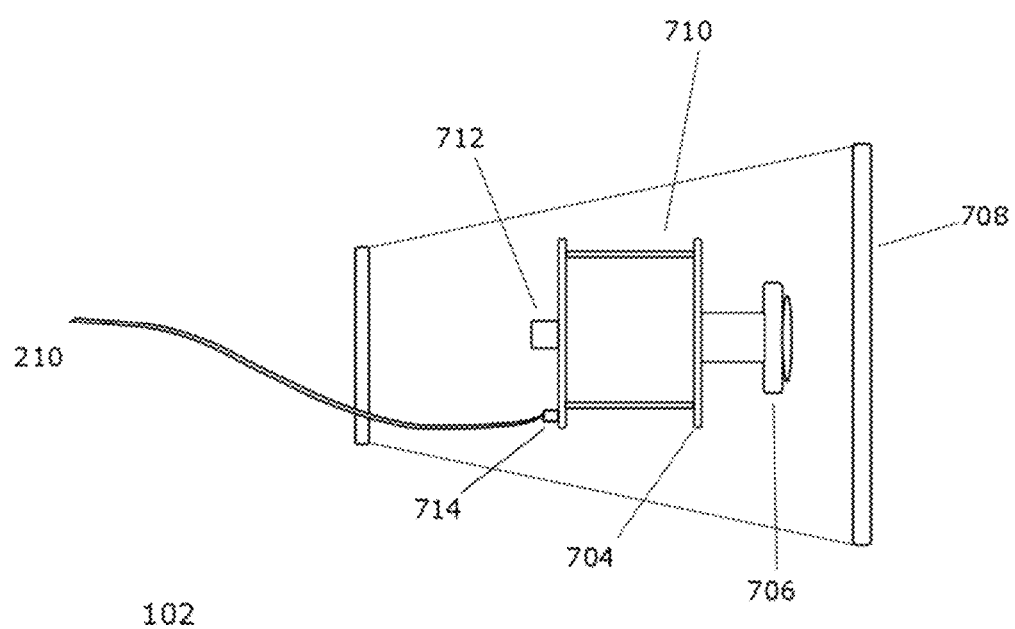
FIG. 7 shows a cross-section of a sensor with optical and inertial sensing components in an electronic guidance system as an example for clarity.

In many surgical procedures, such as THA, care is taken in patient positioning at the beginning of surgery. For example, whether in lateral decubitus or supine positioning, surgeons often ensure that the patient is in a known position with respect to the horizontal plane (referring to the plane orthogonal to gravity). The knowledge of the position of the patient with respect to the horizontal plane is often used as an aid in positioning implants. The ability to electronically measure the horizontal plane has several advantages. This information may be used to aid anatomical registration (i.e. taking advantage of the care taken when positioning patients). The horizontal plane may be registered at the commencement of the surgical procedure, with a low likelihood of the anatomy of the patient having shifted under the surgical draping. The horizontal plane can also be determined by using the plane registration device as described above. Incorporating inclination sensing that can assist in the determination of the horizontal plane may be accomplished, for example, by adding an inclinometer (or accelerometer) into the sensor, as depicted in FIG. 7. The sensor 102 comprises an optical sensor (a camera 704 comprising a lens 706, an optical window 708, etc.) that is connected by a rigid structure 710 to an inclinometer 712. The sensor 102 is also connected via a connector 714 and a cable 210 to a workstation 106. In this case, the sensor 102 provides optical and inclination measurements, both related to a common frame of reference. Further discussion on how to enable this is provided below.

It may also be possible to calculate the orientation of the arbitrary plane using inclination measurements. The sensor may further comprise an inclinometer that captures inclination measurements that can be used to calculate a direction of gravity. Gravity is a vector that is perpendicular to a plane. If the arbitrary plane used for the construction of the registration coordinate frame and the image registration coordinate frame is perpendicular to gravity, the intra-operative computing unit of the electronic guidance system can calculate the orientation of the arbitrary plane by using inclination measurements to determine a direction of gravity.

If the patient is positioned in the same or substantially similar orientation with respect to the arbitrary plane pre-operatively (to obtain medical images) and intra-operatively (for image-guided surgical navigation), the electronic guidance system can utilize properties of the medical image data along with other intra-operative measurements captured by the electronic guidance system to construct the image registration coordinate frame. It is important that the patient's orientation with respect to the arbitrary plane during the pre-operative scan when medical images are captured is substantially similar to the patient's orientation with respect to the same plane when the intra-operative computing unit is constructing the image registration coordinate frame in up to 6 degrees of freedom in accordance with the steps described above.

After the image registration coordinate frame is constructed, the patient may move or shift, purposely or unintentionally, on a surgical table without affecting the registration coordinate frame, the image registration coordinate frame or the surgical measurements provided by the electronic guidance system for image-guided surgical navigation. The system calculates all measurements with reference to the reference element that is attached to the patient's anatomy. As described above, the reference element may be a target or the sensor.

Figure 8:
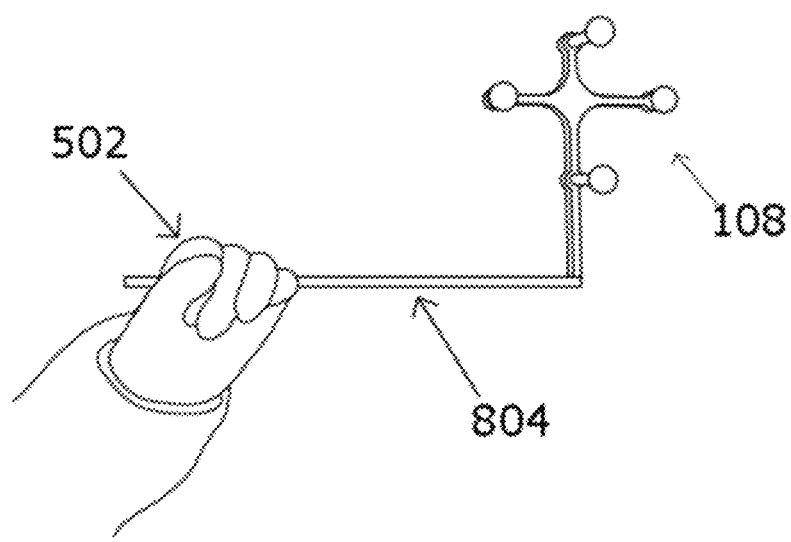
FIG. 8 shows an axis frame with a single axis as an example for clarity.

Often, three degrees of freedom in orientation are needed to register the anatomy. Inclination measurements provide two degrees of freedom in orientation. The inclination measurements may be used for construction of the registration coordinate frame. For example, if an anatomy of a patient has a known position with respect to the horizontal plane, the sensor (attached to the anatomy or to a stable location, such as, the operating table) measures the horizontal plane, and the intra-operative computing unit uses this information as part of anatomical registration. Using inclination measurements to provide up to two degrees of freedom, the third degree of freedom may be measured from an axis frame, configured to provide a single axis. As in FIG. 8, a hand 502 of a user is shown holding an axis frame 202 with a single axis 804 and a target 108 attached to it. During registration, the single axis may be aligned anywhere within the plane of the final degree of freedom. It may be the case that the anatomy of the patient has a known position with respect to only one degree of freedom of the horizontal plane. In this case, two additional degrees of freedom from an axis frame may be required to enable registration of the anatomy. The axis frame with a single axis and a target affixed to it may define at least two degrees of freedom in orientation. The registration coordinate frame may then be constructed by utilizing all three degrees of freedom.

Furthermore, it may be beneficial to generate redundant information required for the registration step. Redundant information can be obtained from a full registration using an axis frame and inclination measurements to capture the same degrees of freedom. Redundant registration information may be beneficial for error checking, or for using an optimization routine to register the anatomy of the patient based on the aggregate information. This information, in the form of a metric, may be displayed to the user or may be used to represent the consistency between the measurements obtained from the inclination system and the optical sensor.

According to a preferred method wherein inclination measurements and optical measurements are used to define a registration, the inclination measurements and the optical measurements may be captured or measured substantially contemporaneously.

An axis may also be defined by capturing (or "localizing") two discrete points. A registration device such as a probe, with a tip that is in a known positional relationship with the target affixed to it, may be used to determine the location of two or more anatomical features of interest. The position of the tip of the probe may be captured by the electronic guidance system as a part of the registration of the anatomy.

The two discrete points (in three-dimensional space) localized by the probe define a vector (analogous to how any one axis of an axis frame defines a vector). For example, the discrete point may be the ASIS (anterior superior iliac spine) of a pelvis, which is a commonly utilized anatomical location for registration.

There are various surgical approaches in THA, such as the posterior approach, anterior approach, etc. that require the patient to be positioned in lateral decubitus or supine. The anterior pelvic plane (APP) of the anatomy is comprised of both ASIS locations and the pubic symphysis, and is often used for registration of the pelvis in different surgical approaches. In image-guided surgery, it is valuable to register the anatomy in six degrees of freedom (DOF) to allow translational and orientational navigation with respect to medical image data of the anatomy. Using the APP by probing two discrete points (usually the left ASIS and right ASIS) on the patient's anatomy while the patient is lying supine facilitates an image registration coordinate frame to be constructed in 6 DOF.

Figure 9:
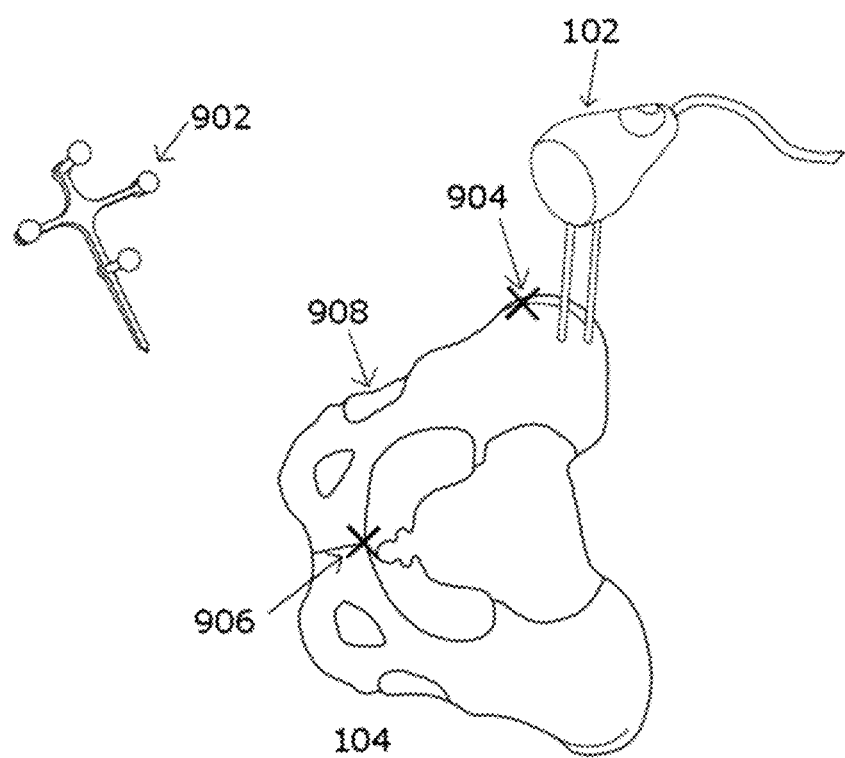
FIG. 9 shows a patient positioned laterally, with a sensor of an electronic guidance system attached to the anatomy of the patient, and a probe to capture locations of landmarks as an example for clarity.

Accessing points that define the anterior pelvic plane can be challenging when a patient is positioned in lateral decubitus, since the location of the contralateral ASIS is obscured and difficult to access for the surgeon. However, if the pelvis is positioned substantially vertically with respect to the operating table or the horizontal plane, this obviates the need to access the contralateral ASIS. It is sufficient to localize two points, such as, the operative ASIS, and the pubis using a probe. These points lie in the frontal plane of the pelvis, and, in combination with inclination measurements (which provide the third degree of freedom), the pelvic registration coordinate frame may be constructed. FIG. 9 illustrates a sensor 102 attached to the pelvis 104 of the patient when the patient is positioned laterally. The target 108 attached to a probe 902 can be used to localize landmarks like the operative ASIS 904 and the pubis 906 or locations within the acetabulum 908. The probe 902 is illustrated to be unitary with the target 108. However, this is not a limitation of this embodiment. The target 108 may be removably attached to the probe 902. The workstation measures the position and orientation of the tip of the probe 902 using positional information from the target 108 to determine the location of the landmarks.

Figure 10:
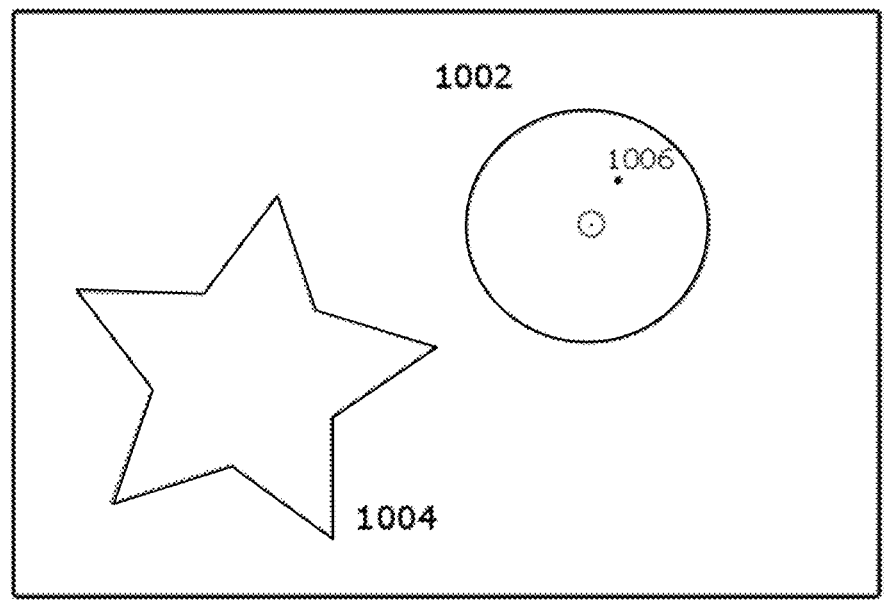
FIG. 10 is a screenshot of a representative bubble level graphic updating in real-time on a display unit of a workstation of an electronic guidance system.

In one embodiment, the inclination measurements of the sensor are provided to the surgeon in real-time to track patient motion during the procedure. These measurements may be provided to a surgeon (e.g. persistently) via the GUI on the display unit. As illustrated in FIG. 10, for example, the measurements may be conveyed as a bubble level graphic 1002 where the graphic may be persistently in real-time or selectively displayed, in addition to other GUI content 1004. The inclination measurements may be displayed relative to the measurements captured during registration such that the bubble 1006 is centered in the graphic 1002 when the current inclination matches the inclination measured at registration. Furthermore, the direction of the bubble level 1006 may utilize the registration coordinate frame such that the current inclination is expressed with respect to the anatomical directions of the body of the patient. As an example, if the bubble moves to the right on the screen, this may have a physical relationship to how the patient may have shifted.

In order to provide inclination measurements, an accelerometer may be integrated within the sensor, as shown in FIG. 7. The optical sensor of the sensor comprises an optical window 708, a camera 704 comprising a lens 706. The accelerometer measurements are combined with optical measurements using techniques known in the art of sensor fusion, such that measurements are provided with a common frame of reference. A rigid structure 710 exists between the location of the camera and the accelerometer, thus creating a rigid mechanical relationship. This relationship is unique for each physical device and is used by the workstation when both the accelerometer 712 and camera 704 communicate measurements to it by any means, e.g. wired through a cable 210, wireless, etc. The workstation may use this relationship to align inclinometer coordinate values to the optical coordinate values, and display further calculations in the same frame of reference.

In addition or alternative to accelerometers, other sensing components may be integrated to assist in registration and/or pose estimation. Such sensing components include, but are not limited to, gyroscopes, inclinometers, magnetometers, etc. It may be preferable for the sensing components to be in the form of electronic integrated circuits.

Both the axis frame and the accelerometer may be used for registration. The optical and inclination measurements captured by the system rely on the surgeon to either accurately position the patient, or accurately align the axis frame along the axis/axes of an anatomy of a patient, or both. It may be desirable to provide further independent information for use in registering the anatomy of the patient. For example, in THA, the native acetabular plane may be registered by capturing the location of at least three points along the acetabular rim using a probe attached to a trackable target. When positioning implants with respect to the pelvis, information may be presented with respect to both registrations—one captured by the workstation from optical measurements of the axis frame and inclination measurements (primary registration coordinate frame), and the other captured by the workstation using the reference plane generated from the optical measurements of the localized landmarks on the acetabular rim of the patient (secondary registration coordinate frame)—either in combination, or independently.

Figure 11:
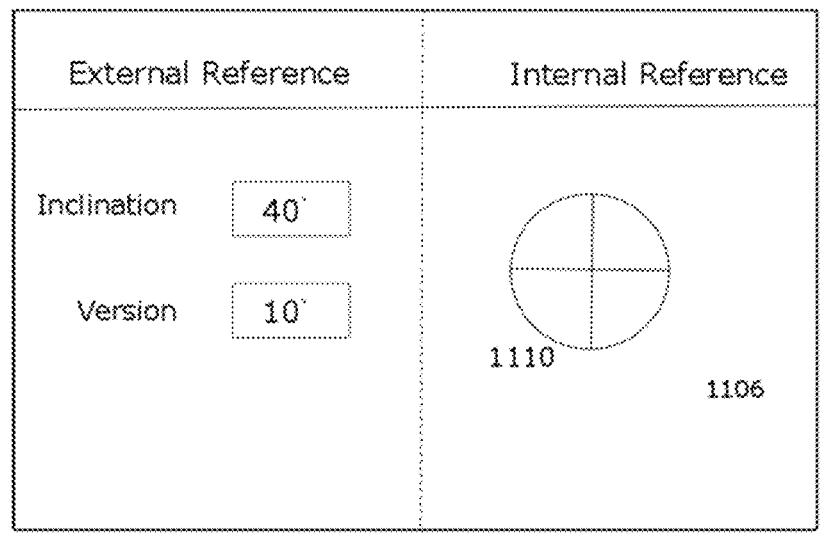
FIG. 11 is a screenshot of a display unit of a workstation showing measurements in internal and external reference coordinate frames in accordance with an embodiment.

FIG. 11 shows a GUI on a display unit. In this embodiment, the interface splits the screen into two sections—an Internal Reference 1102 and an External Reference 1104. The Internal Reference 1102 presents a frame of reference with respect to the internal acetabular landmarks that were independently captured in the construction of the registration coordinate frame as the native anatomy of the patient. A graph 1106 on the GUI displays a bulls-eye indicator 1110 that represents the native acetabulum. The External Reference 1104 presents data to the surgeon in a registration coordinate frame defined by the measuring of the horizontal plane and/or axis frame. The surgeon may use their clinical judgment in interpreting the data and taking appropriate action. In this example, the clinical measurements presented are for real-time acetabular cup alignment in THA.

In the previous embodiments, a sensor has been attached to the anatomy of the patient that is to be registered for the surgical procedure. Each of the previous embodiments may be modified by changing the location of the sensor to another location from which it can detect the position and orientation of one or more targets. For example, the sensor may be attached to an operating table, held in the hand of a surgeon, mounted to a surgeon's head, etc. This embodiment is illustrated in FIG. 12. The sensor 102 is depicted attached to an operating room table 1202. A first target 1204 may be attached to the pelvis 104 of the patient, and a second target 1206 may be attached to a registration device (probe 902 or axis frame 202). The sensor 102 captures the position and orientation of both targets. The workstation calculates a relative measurement of position and orientation between both targets. In addition, the sensor 102 captures the inclination measurements, and the position and orientation of the first target 1204 attached to the anatomy of the patient. The workstation then calculates the direction of the gravity with respect to the first target 1204. Using the relative pose measurement between both targets, and the direction of gravity with respect to the first target 1204 attached to the anatomy of the patient, the workstation can construct the registration coordinate frame.

Figure 13:
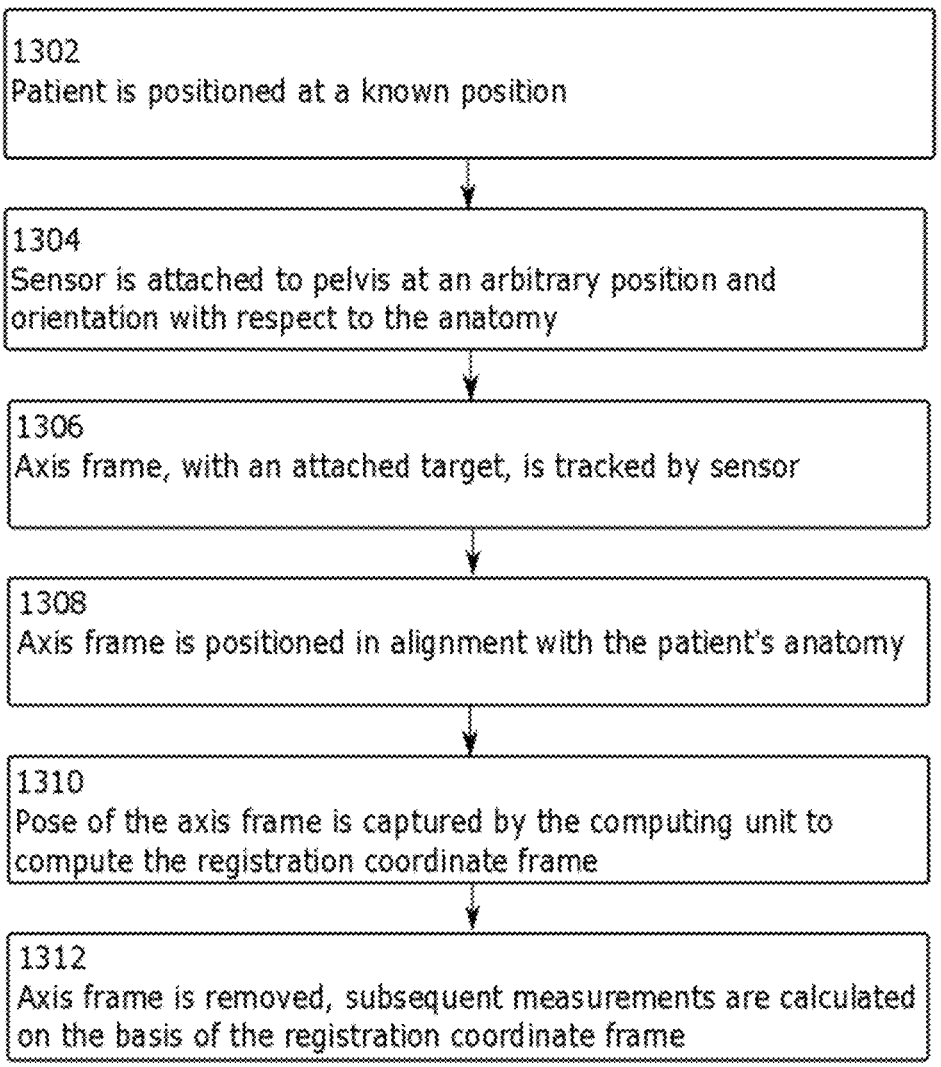
FIG. 13 is a flowchart of a method for registration using a registration device.

An exemplary method of use as shown in the flowchart of FIG. 13 may include the following: at step 1302, a patient is positioned, the position being known to the surgeon. At step 1304, a sensor is rigidly attached to the pelvis at an arbitrary position and orientation with respect to the anatomy. At step 1306, an axis frame, with a trackable target, is tracked by the sensor. At step 1308, when the axis frame is positioned in alignment with the known position of the patient's anatomy by the surgeon, step 1310 is carried out the computing unit to capture the pose of the axis frame by. This pose is used to compute a registration coordinate frame between the sensor and the anatomy. At step 1312, the axis frame is removed and/or discarded, and subsequent positional measurements of the localizer system are calculated on the basis of the registration coordinate frame.

Various methods, devices and systems for anatomical registration are presented herein. The following provides an exemplary workflow illustrating their practical usage in the context of THA. These steps are to provide an exemplary workflow, and not all of the steps are mandatory. For example, if a surgeon is not interested in leg position measurement, the corresponding steps may be omitted.

Figure 14:
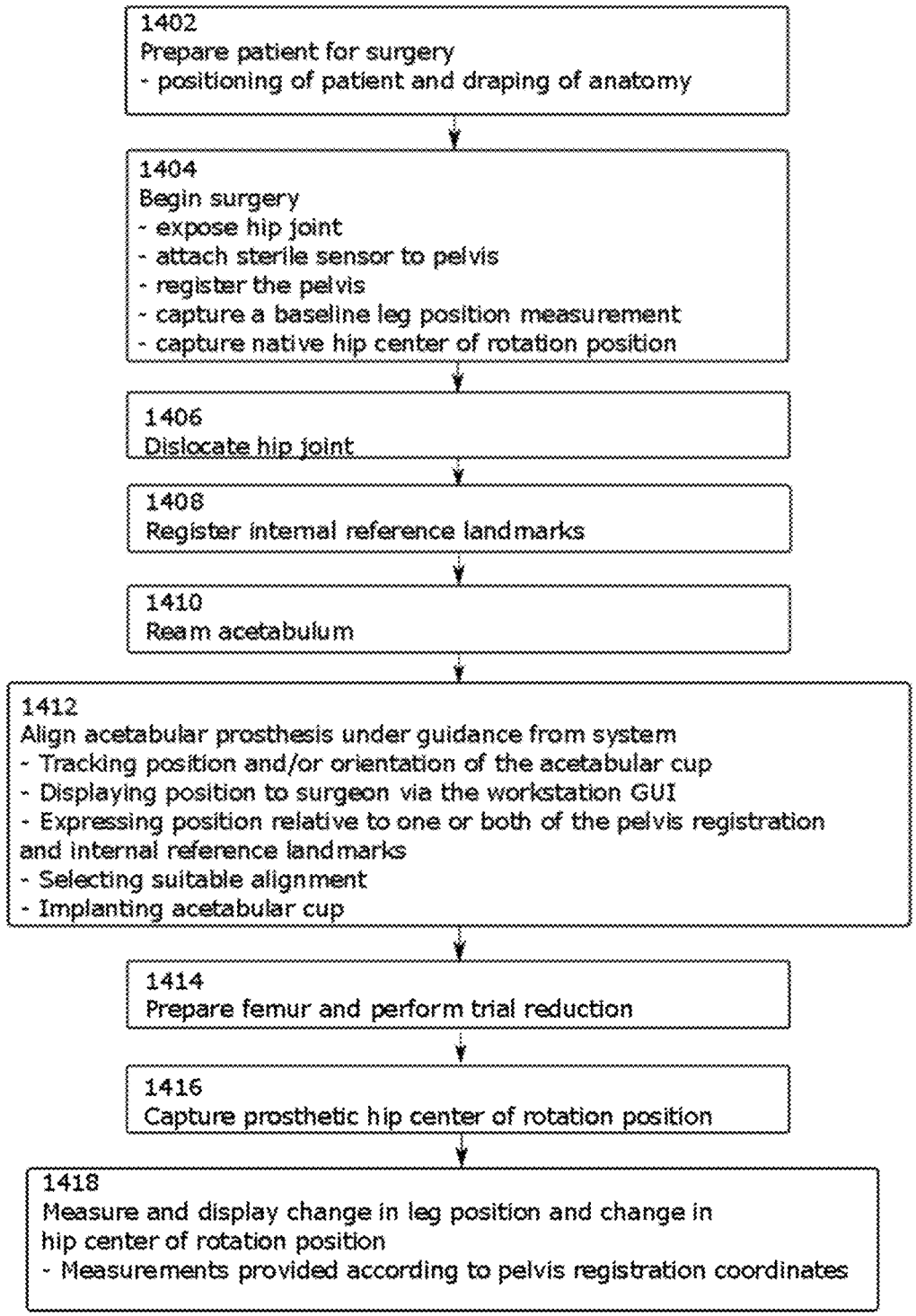
FIG. 14 is a flowchart of a method for total hip arthroplasty using an electronic guidance system in accordance with an embodiment.

As shown in FIG. 14, the flowchart illustrates the steps involved in the overall workflow of THA. The first step 1402 involves preparing a patient for surgery, including positioning and draping. The surgery begins at step 1404 in which the surgeon (in no particular order) attaches the sterile sensor to the pelvis of the patient, registers the pelvis, exposes the hip joint, and captures a baseline leg position measurement and native hip center of rotation position. Those skilled in the art will understand that there are numerous methods, systems and devices available to register the patient and obtain the baseline measurements, some of which are described in the disclosure herein. The next step 1406 is to dislocate the hip joint of the patient. This is followed by step 1408 for registration of internal referencing landmarks, such as, on the acetabular rim. The surgeon then reams the acetabulum at step 1410 to create the surface that will receive the acetabular implant. The surgical navigation system is then used to align the acetabular prosthetic under guidance from the system at step 1412, by tracking the position and/or orientation of the acetabular cup, displaying measurements to the surgeon via the workstation GUI. The measurements may be expressed relative to one or both of the pelvic registration and the internal reference landmarks from the acetabular rim, and selecting a suitable alignment and implanting the acetabular cup.

At step 1414, the surgeon then prepares the femur of the patient and performs trial reductions. During the trials, at step 1416, the surgeon captures a new hip center of rotation position with the prosthetic in place. Finally, at step 1418, the workstation measures and displays change in leg position and change in hip center of rotation position, and the measurements are presented to the surgeon according to the registration coordinate frame.

Figure 15:
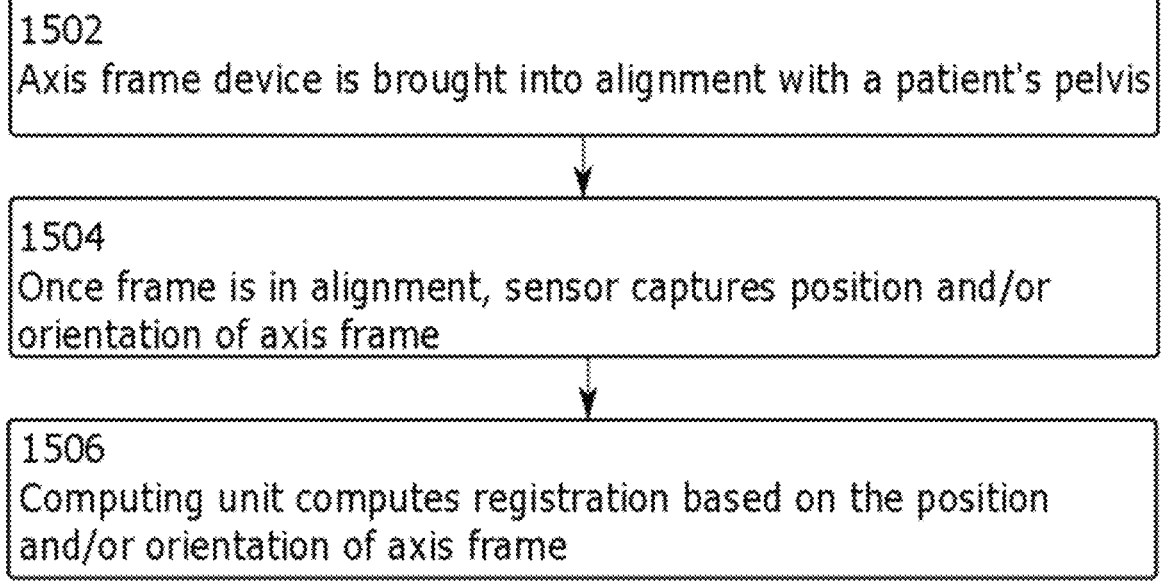
FIG. 15 is a flowchart of a method for registration using an axis frame only in accordance with an embodiment.

In an embodiment, the axis frame can be used in THA as described below in the detailed workflow options for pelvic registration. The method is described in FIG. 15. Using an axis frame at step 1502, the anatomy of the patient can be registered by bringing the axis frame, with the target attached to it, in alignment with the pelvis of the patient while the target is in the field of view of the optical sensor. At step 1504, once the user is satisfied that the axis frame is positioned appropriately with respect to the anatomy of the patient, the user initiates a capture of the position and orientation of the target in up to six degrees of freedom. This could be done, for example, through a human user interface, such as, a button. At step 1506, the intra-operative computing unit utilizes this information and computes a registration coordinate frame for the patient.

Reference is now made to FIG. 16, which illustrates a method of registration. The inclination measurements captured from an inclinometer in the sensor can provide additional measurements to the intra-operative computing unit for constructing the registration coordinate frame. At steps 1602 and 1604, measurements from the axis frame while it is positioned in alignment with the anatomy of the patient are captured and the intra-operative computing unit utilizes these measurements to compute one or two degrees of freedom of the registration measurement. At step 1606, the final degree(s) of freedom is/are captured from the inclinometer when the patient is positioned laterally on an operating table with his/her pelvis orthogonal with respect to the ground. Since the inclinometer can be housed within the optical sensor, there may be a human user interface, such as a button, to capture the optical and inclination measurements simultaneously. The two measurements can also be captured in distinct steps. Using both sets of measurements, at step 1608, the intra-operative computing unit can construct the registration coordinate frame.

Reference is now made to FIG. 17. Instead of using an axis frame to determine an axis of the body of the patient, at step 1702, a probe with an attached target that can be tracked by the optical sensor may be used to localize at least two anatomical landmarks that lie along an anatomical plane (e.g. frontal plane) of the pelvis, e.g.: an operative ASIS and the pubic symphysis. The location of the probe tip is in a known positional relationship with respect to the target. At step 1704, when localizing landmarks, the intra-operative computing unit captures the location of the tip of the probe as it is placed on an anatomical landmark and the optical sensor captures the positional information from the target. While the patient is positioned laterally, i.e. orthogonal to the floor, and the sensor is attached to the body of the patient such that the sensor is upright, inclination measurements are captured (such that the inclination measurements define a plane that represents the sagittal plane of the patient) at step 1706. The intra-operative computing unit is then able to compute the registration coordinate frame in three degrees of freedom based on the two localized landmarks and inclination measurements at step 1708.

Reference is now made to FIG. 18. A computer-implemented method 1800 for a medical navigation guidance system is shown in a flowchart. The method is capable of, at step 1801, measuring a direction of gravity using a sensor 102, the sensor comprising an optical sensor and an inclinometer, attached to an anatomy of a patient positioned in a known orientation with respect to gravity; at step 1802, measuring, by at least one processing unit, a direction of an axis of a device 202, the device 202 having a shape defining at least one axis using positional information in up to six degrees of freedom provided by a target 108 to the optical sensor, and a known positional relationship between the target 108 and the device 202; and at step 1803, constructing, by at least one processing unit, a registration coordinate frame to register, during surgery, the anatomy of the patient based on the direction of gravity, the direction of the axis and the known orientation of the patient with respect to gravity.

Further, as the surgical procedure advances, the target can be attached to a surgical tool and using optical measurements from the optical sensor, the intra-operative computing unit can provide real-time navigation of the surgical tool as it is used by the surgeon. For example, the target may be attached to an acetabular cup impactor and as the impactor is used to install a cup implant in the patient's acetabulum during THA, the system can provide real-time information about position and orientation of the tool to determine angles of the cup implant with respect to the registration coordinate frame or the image registration coordinate frame.

Figure 19A:
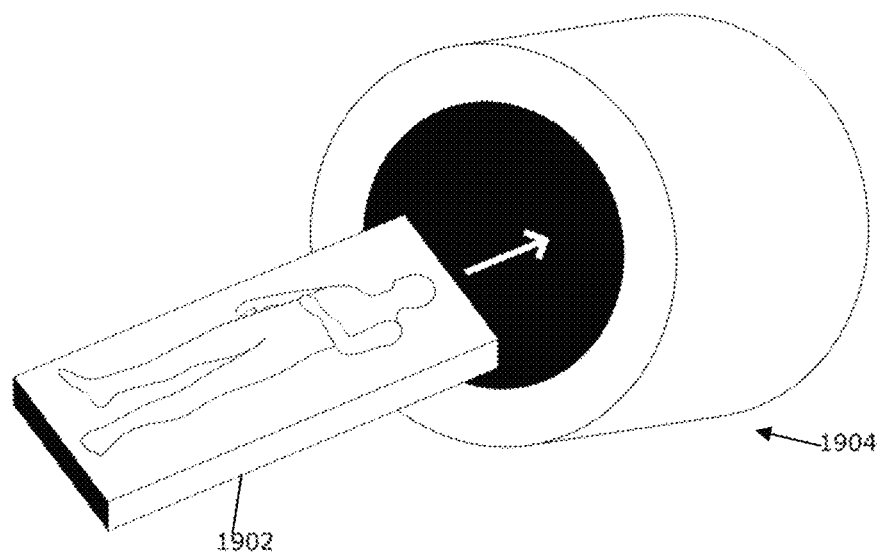
FIG. 19A depicts a patient during a pre-operative CT scan to obtain one or more medical images in accordance with an embodiment.
Figure 19B:
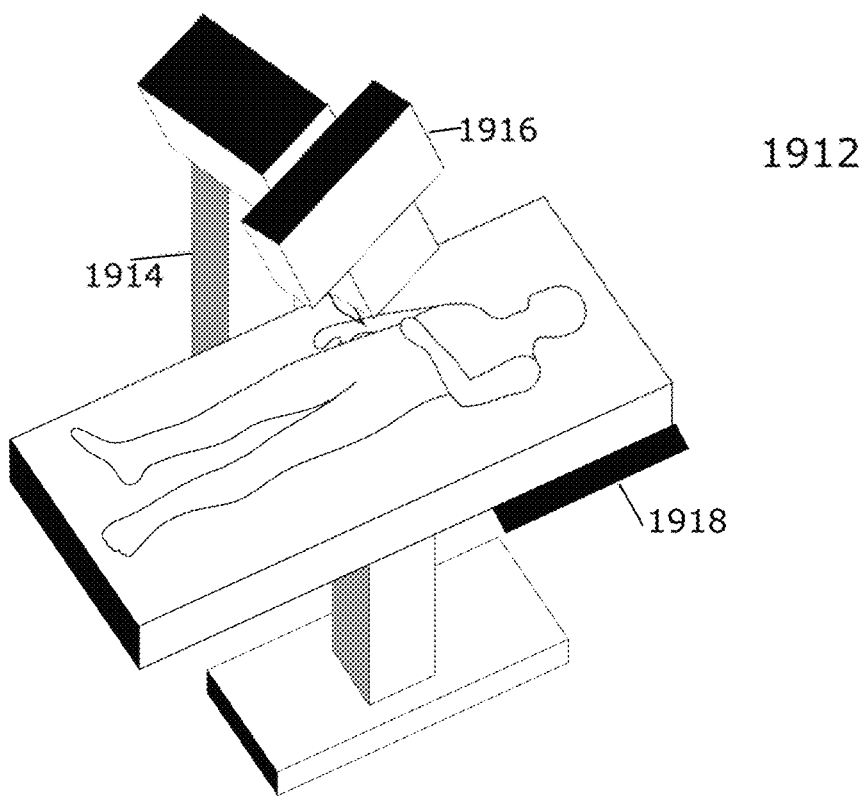
FIG. 19B depicts a patient during a pre-operative X-ray scan to obtain one or more medical images in accordance with an embodiment.

In a THA, surgeons may obtain x-ray, computed tomography (CT) scans, magnetic resonance imaging (MRI) or other scans (that comprise one or more medical images) of a patient's pelvic region. Intra-operatively, it can be helpful to the surgeon to be able to co-relate the anatomical structures that appear on the medical images with the patient's anatomy. Image registration can be used intra-operatively by the electronic guidance system to provide surgical measurements with respect to the medical images of the pre-operative scan. Reference is now made to FIGS. 19A and 19B that depict imaging equipment capturing a pre-operative scan of a patient. In FIG. 19A, a patient is lying supine on a motorized platform 1902 while a CT scanner 1904, the scanner 1904 being exemplary imaging equipment, is used to capture one or more medical images using a rotating X-ray source. During the scan, the patient's anatomy may have a known orientation with respect to an arbitrary plane (e.g. the plane of a mechanical platform or table that is part of the imaging equipment, or the ground). For example, a surgeon or technician may estimate that the patient is positioned as horizontally as possible (horizontal being an example of a common and known patient orientation with respect to the ground). Alternatively, the imaging equipment (and the patient lying on the equipment) may be positioned with a high degree of precision using a digital measurement of tilt with respect to the ground. Intra-operatively, the patient may be positioned in the same or substantially similar orientation with respect to the arbitrary plane.

Reference is now made to FIG. 19B. A patient is lying supine while an X-ray machine 1912 captures 2D x-ray images of the patient's anatomy of interest. It may also be possible to modify an orientation of the x-ray machine 1912 with respect to the arbitrary plane as depicted in FIG. 19B, such that while the patient is lying supine, the machine (such as, an x-ray tube 1914 and collimator 1916) obtains medical images at a second known orientation with respect to the arbitrary plane. There is a cassette 1918 beneath a chest of the patient that obtains the medical images. Other known imaging modalities such as single photon emission computed tomography, positron emission tomography etc. may also be used. The arbitrary plane may have a further known orientation with respect to the direction of gravity. Preferably, the arbitrary plane is perpendicular to gravity. The further known orientation with respect to gravity may be inherent in the imaging equipment (e.g. the mechanical platform is levelled to be parallel to the ground), or may be measured using any suitable means (e.g. a digital level). This further known orientation may be measured using standard equipment that is part of the imaging equipment or may be visually confirmed by a user, for example, special surgical equipment that allows measurement of patient's tilt in one dimension with respect to the ground may be used.

Reference in now made to FIGS. 20A and 20B together depicting a flowchart of a computer-implemented method of image registration without the use of an inclinometer. At step 2001, an intra-operative computing unit receives medical image data of an anatomy of patient, the medical image data is generated from medical images, such medical images made when the patient was in a first known orientation with respect to an arbitrary plane. The medical image data has properties defining a second known orientation of imaging equipment with respect to the arbitrary plane, a direction of an identifiable anatomical axis of the anatomy and a location of an identifiable anatomical point of the anatomy. At step 2002, the computing unit measures a direction of at least one axis of the anatomy with respect to the reference element. The reference element is attached to the anatomy and the patient is positioned in the first known orientation with respect to the arbitrary plane. The computing unit uses optical measurements from a sensor comprising an optical sensor and a target attached to a first registration device. The direction of the axis coincides with the direction of the identifiable anatomical axis of the medical image data. Next, at step 2003, the computing unit measures an orientation of the arbitrary plane with respect to the reference element using optical measurements from the optical sensor generated with the target attached to a plane registration device. At step 2004, the computing unit determines a computed location of at least one point of the anatomy with respect to the reference element. The computing unit uses optical measurements from the optical sensor generated with the target attached to a second registration device, the at least one point coinciding with the identifiable anatomical point of the anatomy in the medical image data. At step 2005, the computing unit constructs a registration coordinate frame to register the anatomy of the patient with respect to the reference element using the orientation of the arbitrary plane and the direction of the axis of the anatomy. At step 2006, the computing unit constructs an image registration coordinate frame to register the anatomy of the patient to the medical image data. The computing unit uses the direction of the identifiable anatomical axis, the location of the identifiable anatomical point of the anatomy, the computed location of at least one point of the anatomy, the orientation of the arbitrary plane, and the second known orientation with respect to the arbitrary plane. At step 2007, the computing unit provides surgical measurements with respect to the medical image data to a display unit in a surgical procedure based on the registration coordinate frame and the image registration coordinate frame.

Reference is now made to FIGS. 21A and 21B together depicting a flowchart of a computer-implemented method of image registration with the use of an inclinometer. At step 2111, an intra-operative computing unit receives medical image data of anatomy of patient, the medical image data is generated from medical images, such medical images made when the patient was in a first known orientation with respect to an arbitrary plane, where the arbitrary plane is perpendicular to gravity. The medical image data has properties defining a second known orientation of imaging equipment with respect to the arbitrary plane, a direction of an identifiable anatomical axis of the anatomy and a location of an identifiable anatomical point of the anatomy. At step 2112, the intra-operative computing unit measures a direction of at least one axis of the anatomy with respect to the reference element. The reference element is attached to the anatomy and the patient is positioned in the first known orientation with respect to the arbitrary plane. The computing unit uses optical measurements from a sensor comprising an optical sensor and a target attached to a first registration device. The direction of the axis coincides with the direction of the identifiable anatomical axis of the medical image data. At step 2113, the computing unit measures an orientation of the arbitrary plane with respect to the reference element using inclination measurements from the sensor, the sensor further comprising an inclinometer. At step 2114, the intra-operative computing unit determines a computed location of at least one point of the anatomy with respect to the reference element. The computing unit uses optical measurements from the optical sensor generated with the target attached to a second registration device, the at least one point coinciding with the identifiable anatomical point of the anatomy in the medical image data. At step 2115, the intra-operative computing unit constructs a registration coordinate frame to register the anatomy of the patient with respect to the reference element using the orientation of the arbitrary plane and the direction of the axis of the anatomy. At step 2116, the intra-operative computing unit constructs an image registration coordinate frame to register the anatomy of the patient to the medical image data. The computing unit uses the direction of the identifiable anatomical axis, the location of the identifiable anatomical point of the anatomy, the computed location of at least one point of the anatomy, the orientation of the arbitrary plane, and the second known orientation with respect to the arbitrary plane. At step 2117, the intra-operative computing unit provides surgical measurements with respect to the medical image data to a display unit in a surgical procedure based on the registration coordinate frame and the image registration coordinate frame.

Careful positioning of the patient in a first known orientation with respect to an arbitrary plane (for example, by positioning the patient horizontally to the ground) pre-operatively and intra-operatively is disclosed herein as a method of ensuring that the patient's orientation is known. This may result in an approximate registration, since any difference in patient orientation in the pre-operative and intra-operative phases may result in inaccuracies. This approximate registration may still be useful as a coarse registration depending on the desire of the surgeon and the requirement of a particular surgical procedure. This registration can also be further fine-tuned with additional measurements that a surgeon captures during the surgical procedure to obtain a fine registration coordinate frame and a fine image registration coordinate frame. These coordinate frames may require the surgeon to localize additional features of the anatomy of the patient to allow the intra-operative computing unit of the electronic guidance system to process additional points to improve accuracy. As an example, this may be done by using one of the registration devices (for example, the probe with a tip) and obtaining optical measurements that correspond to additional anatomical features of the anatomy. In some applications where a highly accurate image registration is required, well known algorithms such as the "iterative closest point" may be used. This algorithm may require an initial coarse registration as a starting point that can be revised iteratively with additional information to obtain a highly accurate image registration.

There are different methods in which medical image data from a pre-operative scan can be used by the electronic guidance system in a surgical procedure. In a first method, the medical image data may be used to perform pre-operative templating to assist the surgeon in determining surgical target parameters to achieve during the surgical procedure. For example, in a THA, the surgeon may calculate particular values for target parameters comprising leg length, offset, inclination and anteversion that would be the most appropriate clinical outcome for the patient. This may be done with the use of dedicated pre-operative planning software. These target parameters would then be compared to surgical measurements obtained from the intra-operative electronic guidance system as described herein. Pre-operatively, the target parameters are obtained by the surgeon in a measured coordinate frame. Intra-operatively, the surgeon delivers the target parameters by comparing surgical measurements from an electronic guidance system in the same measured coordinate frame. This measured coordinate frame may comprise the arbitrary plane and the at least one anatomical direction of the patient's anatomy as described herein.

Figure 22:
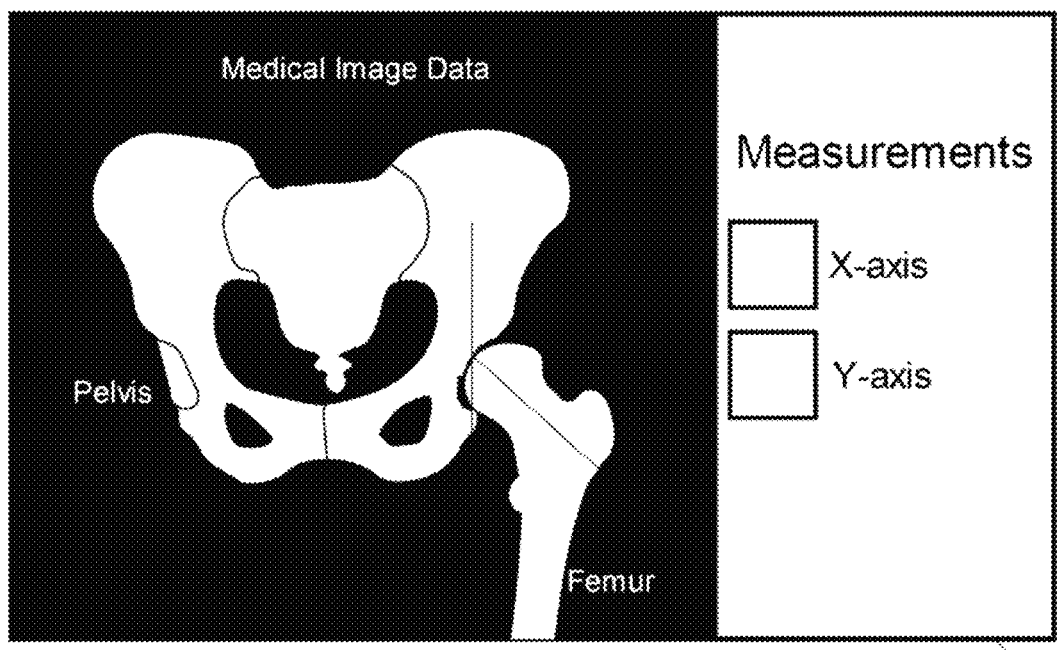
FIG. 22 is a screenshot of a display unit of a workstation showing measurements with respect to a pre-operative scan of the anatomy of the patient.

In a further method, medical image data with properties to define a second known orientation of the imaging equipment with respect to the arbitrary plane, a direction of an identifiable anatomical axis of the anatomy of the patient and a location of an identifiable anatomical point of the anatomy of the patient may be loaded into the intra-operative computing unit. Using optical measurements and optionally, inclination measurements, the electronic guidance system can construct a registration coordinate frame and an image registration coordinate frame. The system may then be used to provide surgical measurements with respect to the patient's anatomy or to the medical image data. The surgical measurements may be displayed on a display unit. FIG. 22 shows a GUI on such a display unit. The interface splits the screen into two sections—the left section showing the one or more medical images captured in the pre-operative scan and the right section showing surgical measurements to the surgeon.

The mathematical operations executed by the intra-operative computing unit to construct the image registration coordinate frame are described broadly as it is understood that from the teaching herein a person of ordinary skill in the art would be able to determine such operations without undo experimentation. The operations described herein are meant to be exemplary, and not limiting. There may be additional or other operations, similar to the ones described below, that can be executed to achieve similar results.

The second known orientation with respect to the arbitrary plane, also defines a plane, and the direction of the identifiable anatomical axis defines a vector. The plane defined by the second known orientation and the vector of the identifiable anatomical axis can be combined to generate a first Cartesian coordinate frame, R1. For example, the Cartesian axes may be generated by using a projection of the vector onto the plane, defining one axis to obtain a first axis; using a vector perpendicular to the plane to obtain a second axis; and performing a cross product of the first axis and the second axis to obtain a third axis.

A second Cartesian coordinate frame, R2 is generated by using the measured orientation of the arbitrary plane and the measured direction of the at least one axis of the anatomy using operations described above, or other linear algebraic operations. A rotation matrix (R') between the first Cartesian coordinate frame R1 and the second Cartesian coordinate frame R2 may be calculated as follows:

$$R1 = R'R2$$

$$R' = R1R2^T, \text{ where } R2^T \text{ is the transpose of } R2$$

Further, a translational vector T can be calculated by subtracting the location of the identifiable anatomical point and the computed location of the at least one point of the anatomy. The rotation matrix R' and the translational vector T are combined in a homogeneous transformation matrix called the image registration matrix, thus constructing the image registration coordinate frame. The registration coordinate frame is also calculated in a similar fashion by applying linear algebraic operations to known and measured values for axes and planes. Measurements from the optical sensor, and optionally the inclinometer, can then be expressed in the image registration coordinate frame by multiplying the sensor measurements by the image registration matrix.

Alternatively, the mathematical operation may be defined as an optimization operation where the plane of the second orientation with respect to the arbitrary plane, the vector of the direction of the identifiable anatomical axis, and the identifiable anatomical point have a fixed positional relationship and are optimized and assigned a first Cartesian coordinate frame. Similarly, a second Cartesian coordinate frame is assigned using the measured orientation of the arbitrary plane, the measured direction of the at least one axis of the anatomy and the computed location of the at least one point of the anatomy. The goal of the optimization operation is to minimize error residual, where the error residual represents a norm between each of the second known orientation of the imaging equipment with respect to the arbitrary plane, the orientation of the arbitrary plane, direction of the identifiable anatomical axis, the direction of the at least one axis of the anatomy, the location of the identifiable anatomical point and the computed location of the at least one point of the anatomy. The optimization variables are the spatial rotations and translations between the first Cartesian coordinate frame and second Cartesian coordinate frame i.e. the result of the optimization is the transformation matrix (rotation/translation) that minimizes the norm between the corresponding features in each of the first Cartesian coordinate frame and second Cartesian coordinate frame. This homogeneous transformation matrix is called the image registration matrix, thus constructing the image registration coordinate frame. Measurements from the optical sensor, and optionally the inclinometer, can then be expressed in the image registration coordinate frame by multiplying the sensor measurements by the image registration matrix.

FIGS. 23A and 23B discuss the two methods of use describe above. In method 2300, at step 2301, a pre-operative scan of a patient's anatomy is obtained with the patient positioned in a first known orientation with respect to an arbitrary plane. One or more medical images of the pre-operative scan are processed to generate medical image data and the surgeon obtains target parameters for the surgical procedure, the target parameters having a known relationship to the arbitrary plane and to an identifiable anatomical direction of the anatomy of the patient. Intra-operatively, at step 2302, the surgeon positions the patient in the first known orientation with respect to the arbitrary plane and invokes a sensor of an electronic guidance system (comprising an optical sensor and optionally, an inclination sensor) to capture a direction of an intra-operative axis of the anatomy of the patient, such that the direction of the intra-operative axis coincides with the identifiable anatomical direction. Next, at step 2303, the surgeon invokes the electronic guidance system to capture an orientation of an intra-operative plane of the anatomy of the patient using the sensor of the electronic guidance system, the orientation of the intra-operative plane coinciding with the arbitrary plane. At step 2304, the surgeon views surgical measurements provided by the electronic guidance system, the measurements provided with respect to the intra-operative plane and the intra-operative axis of the anatomy. And finally, at step 2305, the surgeon performs the surgical procedure while comparing the surgical measurements to the target parameters.

In method 2310 shown in FIG. 23B, at step 2311, a surgeon obtains a pre-operative scan with patient positioned in a first known position with respect to an arbitrary plane and may process medical images captured during a pre-operative scan to create medical image data and obtain target parameters for a surgical procedure. Depending on the surgical procedure, target parameters may be optional. At step 2312, the surgeon may load medical image data and optionally, the target parameters into an intra-operative computing unit of an electronic guidance system. During the surgery, at step 2313, the surgeon registers the patient's anatomy to the electronic guidance system and/or medical image data by capturing optical measurements and optionally, inclination measurements, to the electronic guidance system while the patient is in the first known position with respect to the arbitrary plane. At step 2314, the surgeon can use the electronic guidance system achieve target parameters using the surgical measurements displayed by the electronic guidance system with respect to the medical image data. If the target parameters are not provided to the system, the surgeon may use the surgical measurements for navigation only.

Accordingly, it is to be understood that this subject matter is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible.

What is claimed is:

1. A system comprising:
  a sensor comprising an optical sensor configured to provide optical information, and a measuring sensor configured to provide measurements for determining a direction of gravity;
  a first target configured to attach to an anatomy of a patient and configured to provide positional information in up to six degrees of freedom to the optical sensor;
  a second target configured to attach in a known positional relationship to an object, the second target configured to provide positional information in up to six degrees of freedom to the optical sensor; and
  an intra-operative computing unit configured to:
    receive first optical information for the first target and second target, and measurements for determining the direction of gravity, wherein the first optical information and the measurements received from the sensor are for a registration step performed for a registration, the first optical information comprising information for the second target attached to a registration device to determine at least one axis relative to the anatomy;
    receive second optical information for the first target and second target, the second optical information received from the sensor for a subsequent step of a surgical procedure, the second optical information comprising information for the second target attached to a bone of the anatomy of the patient, a surgical tool for the surgical procedure, or an implant for the surgical procedure; and determine and present measurements relative to the anatomy for the surgical procedure, wherein the measurements relative to the anatomy are determined from the second optical information, and in relation to the registration of the anatomy of the patient.

2. The system of claim 1, wherein the intra-operative computing unit is configured to determine a registration coordinate frame for the anatomy of the patient based on the direction of gravity, the position and orientation of the first target and the at least one axis for the registration step.

3. The system of claim 1 comprising the registration device.

4. The system of claim 1, wherein the registration device comprises an elongate element configured to extend along an axis of the anatomy.

5. The system of claim 1, wherein the registration device comprises a probe tip configured to contact an anatomical point of the anatomy.

6. The system of claim 5, wherein the known positional relationship is between the second target and the probe tip.

7. The system of claim 6, wherein:
the first optical information comprises information identifying respective locations of two or more anatomical features of the anatomy of the patient; and
the intra-operative computing unit is configured to determine the at least one axis using the known positional relationship and the respective locations of the two or more anatomical features.

8. The system of claim 7, wherein two of the two or more anatomical features lie on an anterior pelvic plane (APP) of the anatomy.

9. The system of claim 8, wherein the two of the two or more anatomical features are a left anterior superior iliac spine (ASIS) and a right ASIS.

10. The system of claim 1, wherein the second target is removably attachable to the registration device.

11. The system of claim 1, wherein the sensor comprises a handheld sensor to be held in a hand of a user.

12. The system of claim 1, wherein the sensor is configured to provide the optical information and the measurements for determining the direction of gravity relative to a common frame of reference.

13. The system of claim 1, wherein the anatomy to which the first target is attached is positioned in a known orientation with respect to the direction of gravity.

14. The system of claim 1, comprising a display screen and wherein the intra-operative computing unit is configured to present the measurements relative to the anatomy for display by the display screen.

15. The system of claim 14, wherein the anatomy is a pelvis, and wherein the surgical procedure is a Total Hip Arthroplasty (THA).

16. The system of claim 15, wherein the measurements relative to the anatomy comprise clinical measurements for real-time acetabular cup alignment in THA.

17. The system of claim 1, wherein the measuring sensor comprises any one or more of an inclinometer, an accelerometer, a gyroscope and a magnetometer.

18. A system comprising:
a first target configured to attach to a pelvis of a patient, the first target configured to provide positional information in up to six degrees of freedom to the optical sensor;

a second target configured to attach in a known positional relationship to an object, the second target configured to provide positional information in up to six degrees of freedom to the optical sensor, the object comprising a femur, a surgical tool or an implant;

a handheld registration device configured to define at least one axis of an anatomy of the patient;

a handheld sensor comprising an optical sensor configured to provide optical information and a measuring sensor configured to provide measurements for determining a direction of gravity; and an intra-operative computing unit configured to:
receive, from the handheld sensor, first optical information for the first target and second target, and first measurements for determining the direction of gravity, the first optical information and the first measurements received for a registration step to perform a registration, the first optical information comprising information for the second target attached to the registration device to determine at least one axis relative to the anatomy;

receive, from the handheld sensor, second optical information for the first target and second target for a subsequent step of a surgical procedure, the second optical information comprising information for the second target attached to the femur of the patient, the surgical tool comprising an implant tool for a THA procedure or the implant for the THA procedure; and determine and present measurements relative to the anatomy for the surgical procedure, wherein the measurements relative to the anatomy are determined from the second optical information, and in relation to the registration of the anatomy of the patient.

19. The system of claim 18, wherein the registration device comprises: i) an elongate element configured to extend along an axis of the anatomy to define the axis; or ii) a probe tip configured for contacting respective locations of two or more anatomical features for defining the axis.

20. A computer implemented method executed by a processor of an intra-operative computing unit, the method comprising:
receiving, from a sensor, first optical information for a first target and a second target, and measurements for determining a direction of gravity for a registration step to perform a registration of an anatomy of a patient, the first optical information comprising information for: i) the first target attached to the anatomy of the patient; and ii) the second target attached to a registration device to determine at least one axis relative to the anatomy of the patient, and wherein each of the first target and the second target is configured to provide positional information in up to six degrees of freedom to an optical sensor configured to provide optical information, and wherein the sensor comprises the optical sensor, and a measuring sensor, the measuring sensor configured to provide measurements for determining the direction of gravity;

receiving, from the sensor, second optical information for the first target and second target, the second optical information received for a subsequent step of a surgical procedure, the second optical information comprising information for the second target attached to a bone of the anatomy of the patient, a surgical tool for the surgical procedure, or an implant for the surgical procedure; and determining and presenting measurements relative to the anatomy of the patient for the surgical procedure, wherein the measurements relative to the anatomy of the patient are determined from the second optical information, and in relation to the registration of the anatomy of the patient.

* * * * *